(12) United States Patent
Finnestad et al.

(10) Patent No.: US 8,628,497 B2
(45) Date of Patent: Jan. 14, 2014

(54) SAFETY CATHETER

(71) Applicants: Mark B. Finnestad, Franklin, MA (US); Steven A. Holley, Cumming, GA (US)

(72) Inventors: Mark B. Finnestad, Franklin, MA (US); Steven A. Holley, Cumming, GA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/625,957

(22) Filed: Sep. 25, 2012

(65) Prior Publication Data

US 2013/0079720 A1    Mar. 28, 2013

Related U.S. Application Data

(60) Provisional application No. 61/539,129, filed on Sep. 26, 2011.

(51) Int. Cl.
 *A61M 5/178* (2006.01)
(52) U.S. Cl.
 USPC ............................... 604/164.08; 604/164.01
(58) Field of Classification Search
 USPC ................ 604/110, 164.01, 164.08, 192
 See application file for complete search history.

(56) References Cited

U.S. PATENT DOCUMENTS

| | | | |
|---|---|---|---|
| 3,134,380 A | 5/1964 | Armao |
| 3,884,230 A | 5/1975 | Wulff |
| 4,387,879 A | 6/1983 | Tauschinski |
| 4,512,766 A | 4/1985 | Vailancourt |
| 4,725,267 A | 2/1988 | Vaillancourt |
| 4,755,170 A | 7/1988 | Golden |
| 4,778,453 A | 10/1988 | Lopez |
| 4,795,432 A | 1/1989 | Karczmer |
| 4,804,370 A | 2/1989 | Haber |
| 4,804,371 A | 2/1989 | Vaillancourt |
| 4,808,169 A | 2/1989 | Haber |
| 4,834,718 A | 5/1989 | Mc donald |
| 4,842,591 A | 6/1989 | Luther |
| 4,846,805 A | 7/1989 | Sitar |
| 4,850,977 A | 7/1989 | Bayless |
| 4,850,994 A | 7/1989 | Zerbst |
| 4,863,434 A | 9/1989 | Bayless |

(Continued)

FOREIGN PATENT DOCUMENTS

| | | |
|---|---|---|
| WO | WO 2010/061405 | 6/2010 |
| WO | WO 2011/036574 | 3/2011 |
| WO | WO 2011/154767 | 12/2011 |
| WO | WO 2012/014018 | 2/2012 |

OTHER PUBLICATIONS

U.S. Appl. No. 13/616,464, filed Sep. 14, 2012, Tremblay.
U.S. Appl. No. 13/625,957, filed Sep. 25, 2012, Finnestad et al.

(Continued)

*Primary Examiner* — Nicholas Lucchesi
*Assistant Examiner* — Leah Stohr
(74) *Attorney, Agent, or Firm* — Lisa E. Winsor, Esq.

(57) ABSTRACT

A needle assembly including a needle tip guard and needle is provided. The needle tip guard includes a proximal base defining an opening that is dimensioned for passage of the needle therethrough, first and second clamp members extending from the proximal base and defining an internal cavity, and a finger tab extending from the proximal base. Each of the first and second clamp members define an inner surface including a protrusion extending into the internal cavity. A distal end of each of the clamp members includes a clamp arm, the clamp arms being supported for movement between an open position and a closed position. The finger tab includes a contacting portion for engagement by a user.

14 Claims, 4 Drawing Sheets

(56) References Cited

U.S. PATENT DOCUMENTS

| | | |
|---|---|---|
| 4,863,436 A | 9/1989 | Glick |
| 4,867,746 A | 9/1989 | Dufresne |
| 4,874,377 A | 10/1989 | Newgard |
| 4,908,022 A | 3/1990 | Haber |
| 4,909,794 A | 3/1990 | Haber |
| 4,911,706 A | 3/1990 | Levitt |
| 4,917,668 A | 4/1990 | Haindl |
| 4,921,486 A | 5/1990 | De chellis |
| 4,921,490 A | 5/1990 | Spier |
| 4,927,415 A | 5/1990 | Brodsky |
| 4,929,241 A | 5/1990 | Kulli |
| 4,931,040 A | 6/1990 | Haber |
| 4,935,010 A | 6/1990 | Cox |
| 4,944,723 A | 7/1990 | Haber |
| 4,944,728 A | 7/1990 | Carrell |
| 4,952,207 A | 8/1990 | Lemieux |
| 4,955,866 A | 9/1990 | Corey |
| 4,964,854 A | 10/1990 | Luther |
| 4,978,343 A | 12/1990 | Dysarz |
| 4,978,344 A | 12/1990 | Dombrowski |
| 4,986,813 A | 1/1991 | Blake, III |
| 4,986,819 A | 1/1991 | Sobel |
| 4,994,041 A | 2/1991 | Dombrowski |
| 4,994,046 A | 2/1991 | Wesson |
| 4,998,922 A | 3/1991 | Kuracina |
| 5,002,533 A | 3/1991 | Jullien |
| 5,013,305 A | 5/1991 | Opie |
| 5,015,234 A | 5/1991 | Jullien |
| 5,015,240 A | 5/1991 | Soproni |
| 5,015,241 A | 5/1991 | Feimer |
| 5,015,242 A | 5/1991 | Heifetz |
| 5,030,208 A | 7/1991 | Novacek |
| 5,049,136 A | 9/1991 | Johnson |
| 5,051,109 A | 9/1991 | Simon |
| 5,053,014 A | 10/1991 | Van heugten |
| 5,053,017 A | 10/1991 | Chamuel |
| 5,059,180 A | 10/1991 | Mclees |
| 5,059,184 A | 10/1991 | Dyke |
| 5,080,651 A | 1/1992 | Julien |
| 5,084,018 A | 1/1992 | Tsao |
| 5,085,648 A | 2/1992 | Purdy |
| 5,092,461 A | 3/1992 | Adam |
| 5,092,851 A | 3/1992 | Ragner |
| 5,104,378 A | 4/1992 | Haber |
| 5,112,311 A | 5/1992 | Utterberg |
| 5,114,404 A | 5/1992 | Paxton |
| 5,120,321 A | 6/1992 | Oksman |
| 5,122,118 A | 6/1992 | Haber |
| 5,122,124 A | 6/1992 | Novacek |
| 5,127,905 A | 7/1992 | Lemieux |
| 5,131,405 A | 7/1992 | Burns |
| 5,135,504 A | 8/1992 | Mc lees |
| 5,137,515 A | 8/1992 | Hogan |
| 5,147,327 A | 9/1992 | Johnson |
| 5,154,699 A | 10/1992 | Ryan |
| 5,154,703 A | 10/1992 | Bonaldo |
| 5,156,596 A | 10/1992 | Balbierz |
| 5,158,554 A | 10/1992 | Jepson |
| 5,169,391 A | 12/1992 | Vogel |
| 5,171,229 A | 12/1992 | Mc neil |
| 5,171,300 A | 12/1992 | Blake, III |
| 5,176,650 A | 1/1993 | Haining |
| 5,176,655 A | 1/1993 | Mc cormick |
| 5,176,656 A | 1/1993 | Bayless |
| 5,180,369 A | 1/1993 | Dysarz |
| 5,180,370 A | 1/1993 | Gillespie |
| 5,183,468 A | 2/1993 | Mclees |
| 5,188,607 A | 2/1993 | Wu |
| 5,195,723 A | 3/1993 | Schauerte |
| 5,195,974 A | 3/1993 | Hardy |
| 5,195,980 A | 3/1993 | Catlin |
| 5,199,947 A | 4/1993 | Lopez |
| 5,205,827 A | 4/1993 | Novacek |
| 5,205,829 A | 4/1993 | Lituchy |
| 5,207,656 A | 5/1993 | Kranys |
| 5,211,629 A | 5/1993 | Pressly |
| 5,211,633 A | 5/1993 | Stouder, Jr. |
| 5,215,525 A | 6/1993 | Sturman |
| 5,215,528 A | 6/1993 | Purdy |
| 5,215,533 A | 6/1993 | Robb |
| 5,215,534 A | 6/1993 | De harde |
| 5,215,538 A | 6/1993 | Larkin |
| 5,222,505 A | 6/1993 | Burns |
| 5,224,936 A | 7/1993 | Gallagher |
| 5,228,646 A | 7/1993 | Raines |
| 5,232,456 A | 8/1993 | Gonzalez |
| 5,232,458 A | 8/1993 | Chen |
| 5,234,410 A | 8/1993 | Graham |
| 5,242,393 A | 9/1993 | Brimball |
| 5,242,400 A | 9/1993 | Blake, III |
| 5,242,402 A | 9/1993 | Chen |
| 5,242,411 A | 9/1993 | Yamamoto |
| 5,246,427 A | 9/1993 | Sturman |
| RE34,416 E | 10/1993 | Lemieux |
| 5,251,873 A | 10/1993 | Atkinson |
| 5,254,099 A | 10/1993 | Kuracina |
| 5,256,152 A | 10/1993 | Marks |
| 5,261,880 A | 11/1993 | Streck |
| 5,261,894 A | 11/1993 | Smith |
| 5,263,933 A | 11/1993 | Novacek |
| 5,266,072 A | 11/1993 | Utterberg |
| 5,267,966 A | 12/1993 | Paul |
| 5,267,976 A | 12/1993 | Guerineau |
| 5,269,763 A | 12/1993 | Boehmer |
| 5,269,764 A | 12/1993 | Vetter |
| 5,269,765 A | 12/1993 | Kuracina |
| 5,269,771 A | 12/1993 | Thomas |
| 5,273,540 A | 12/1993 | Luther |
| 5,277,342 A | 1/1994 | Dickau |
| 5,279,570 A | 1/1994 | Dombrowski |
| 5,279,571 A | 1/1994 | Larkin |
| 5,279,591 A | 1/1994 | Simon |
| 5,290,246 A | 3/1994 | Yamamoto |
| 5,293,970 A | 3/1994 | Schneider |
| 5,295,657 A | 3/1994 | Atkinson |
| 5,295,658 A | 3/1994 | Atkinson |
| 5,295,963 A | 3/1994 | Deeks |
| 5,295,972 A | 3/1994 | Mischenko |
| 5,297,777 A | 3/1994 | Yie |
| 5,300,032 A | 4/1994 | Hibbs |
| 5,300,033 A | 4/1994 | Miller |
| 5,300,034 A | 4/1994 | Behnke |
| 5,300,035 A | 4/1994 | Clement |
| 5,300,040 A | 4/1994 | Martin |
| 5,300,045 A | 4/1994 | Plassche, Jr. |
| 5,304,136 A | 4/1994 | Erskine |
| 5,304,151 A | 4/1994 | Kuracina |
| 5,304,156 A | 4/1994 | Sylvanowicz |
| 5,306,243 A | 4/1994 | Bonaldo |
| 5,308,336 A | 5/1994 | Hart |
| 5,312,355 A | 5/1994 | Lee |
| 5,312,362 A | 5/1994 | Pfolsgraf |
| 5,312,363 A | 5/1994 | Ryan |
| 5,312,371 A | 5/1994 | Dombrowski |
| 5,312,372 A | 5/1994 | De harde |
| 5,322,517 A | 6/1994 | Sircom |
| 5,322,518 A | 6/1994 | Schneider |
| 5,324,271 A | 6/1994 | Abiuso |
| 5,328,478 A | 7/1994 | Mcvay |
| 5,328,482 A | 7/1994 | Sircom |
| 5,328,484 A | 7/1994 | Somers |
| 5,328,485 A | 7/1994 | Moreno |
| 5,330,435 A | 7/1994 | Vaillancourt |
| 5,330,437 A | 7/1994 | Durman |
| 5,334,158 A | 8/1994 | Mc lees |
| 5,334,159 A | 8/1994 | Turkel |
| 5,336,192 A | 8/1994 | Palestrant |
| 5,336,198 A | 8/1994 | Silver |
| 5,336,199 A | 8/1994 | Castillo |
| 5,336,200 A | 8/1994 | Streck |
| 5,342,316 A | 8/1994 | Wallace |
| 5,342,319 A | 8/1994 | Watson |
| 5,344,161 A | 9/1994 | Sandgren |
| 5,344,408 A | 9/1994 | Partika |

(56) References Cited

U.S. PATENT DOCUMENTS

| | | |
|---|---|---|
| 5,344,414 A | 9/1994 | Lopez |
| 5,348,544 A | 9/1994 | Sweeney |
| 5,350,362 A | 9/1994 | Stouder, Jr. |
| 5,350,363 A | 9/1994 | Goode |
| 5,352,205 A | 10/1994 | Dales |
| 5,353,837 A | 10/1994 | Faust |
| 5,354,280 A | 10/1994 | Haber |
| 5,356,384 A | 10/1994 | Haber |
| 5,360,413 A | 11/1994 | Leason |
| 5,364,370 A | 11/1994 | Szerlip |
| 5,364,372 A | 11/1994 | Danks |
| 5,368,574 A | 11/1994 | Antonacci |
| 5,376,077 A | 12/1994 | Gomringer |
| 5,380,288 A | 1/1995 | Hart |
| 5,380,305 A | 1/1995 | Ghouri |
| 5,382,235 A | 1/1995 | Sak |
| 5,383,860 A | 1/1995 | Lau |
| 5,385,550 A | 1/1995 | Su |
| 5,389,081 A | 2/1995 | Castro |
| 5,390,898 A | 2/1995 | Smedley |
| 5,395,338 A | 3/1995 | Gaba |
| 5,395,346 A | 3/1995 | Maggioni |
| 5,395,347 A | 3/1995 | Blecher |
| 5,395,352 A | 3/1995 | Penny |
| 5,403,284 A | 4/1995 | Gross |
| 5,405,323 A | 4/1995 | Rogers |
| 5,405,327 A | 4/1995 | Chen |
| 5,405,331 A | 4/1995 | Behnke |
| 5,409,461 A | 4/1995 | Steinman |
| 5,409,464 A | 4/1995 | Villalobos |
| 5,411,486 A | 5/1995 | Zadini |
| 5,411,492 A | 5/1995 | Sturman |
| 5,415,638 A | 5/1995 | Novacek |
| 5,417,659 A | 5/1995 | Gaba |
| 5,417,673 A | 5/1995 | Gordon |
| 5,419,766 A | 5/1995 | Chang |
| 5,423,766 A | 6/1995 | Cesare |
| 5,425,718 A | 6/1995 | Tay |
| 5,425,720 A | 6/1995 | Rogalsky |
| 5,429,596 A | 7/1995 | Arias |
| 5,429,619 A | 7/1995 | Furnish |
| 5,431,631 A | 7/1995 | Lu |
| 5,431,632 A | 7/1995 | Lu |
| 5,433,703 A | 7/1995 | Utterberg |
| 5,437,646 A | 8/1995 | Hunt |
| 5,439,451 A | 8/1995 | Collinson |
| 5,441,487 A | 8/1995 | Vedder |
| 5,443,452 A | 8/1995 | Hart |
| 5,443,454 A | 8/1995 | Tanabe |
| 5,447,501 A | 9/1995 | Karlsson |
| 5,453,095 A | 9/1995 | Davila |
| 5,454,790 A | 10/1995 | Dubrul |
| 5,456,284 A | 10/1995 | Ryan |
| 5,456,675 A | 10/1995 | Wolbring |
| 5,458,640 A | 10/1995 | Gerrone |
| 5,458,658 A | 10/1995 | Sircom |
| 5,460,603 A | 10/1995 | Desantis |
| 5,462,531 A | 10/1995 | Novacek |
| 5,465,938 A | 11/1995 | Werge |
| 5,466,223 A | 11/1995 | Bressler |
| 5,466,230 A | 11/1995 | Davila |
| 5,470,319 A | 11/1995 | Mayer |
| 5,472,418 A | 12/1995 | Palestrant |
| 5,474,544 A | 12/1995 | Lynn |
| 5,478,313 A | 12/1995 | White |
| 5,480,393 A | 1/1996 | Bommarito |
| 5,484,401 A | 1/1996 | Rodriguez |
| 5,486,190 A | 1/1996 | Green |
| 5,487,728 A | 1/1996 | Vaillancourt |
| 5,487,733 A | 1/1996 | Caizza |
| 5,487,850 A | 1/1996 | Vanderploeg |
| 5,489,274 A | 2/1996 | Chu |
| 5,492,147 A | 2/1996 | Challender |
| 5,492,304 A | 2/1996 | Smith |
| 5,496,274 A | 3/1996 | Graves |
| 5,496,280 A | 3/1996 | Vandenbroek |
| 5,501,426 A | 3/1996 | Atkinson |
| 5,501,670 A | 3/1996 | Sak |
| 5,501,675 A | 3/1996 | Erskine |
| 5,507,732 A | 4/1996 | Mcclure |
| 5,509,433 A | 4/1996 | Paradis |
| 5,514,098 A | 5/1996 | Pfoslgraf |
| 5,514,116 A | 5/1996 | Vaillancourt |
| 5,514,117 A | 5/1996 | Lynn |
| 5,520,649 A | 5/1996 | Novacek |
| 5,520,655 A | 5/1996 | Davila |
| 5,520,666 A | 5/1996 | Choudhury |
| 5,531,701 A | 7/1996 | Luther |
| 5,533,974 A | 7/1996 | Gaba |
| 5,533,975 A | 7/1996 | Lu |
| 5,535,785 A | 7/1996 | Werge |
| 5,538,505 A | 7/1996 | Weinstein |
| 5,538,508 A | 7/1996 | Steyn |
| 5,540,661 A | 7/1996 | Tomisaka |
| 5,540,662 A | 7/1996 | Nicholson |
| 5,545,146 A | 8/1996 | Ishak |
| 5,545,152 A | 8/1996 | Funderburk |
| 5,549,565 A | 8/1996 | Ryan |
| 5,549,566 A | 8/1996 | Elias |
| 5,549,570 A | 8/1996 | Rogalsky |
| 5,549,576 A | 8/1996 | Patterson |
| 5,549,651 A | 8/1996 | Lynn |
| 5,554,131 A | 9/1996 | Lacivita |
| 5,558,651 A | 9/1996 | Crawford |
| 5,562,629 A | 10/1996 | Haughton |
| 5,562,630 A | 10/1996 | Nichols |
| 5,562,632 A | 10/1996 | Davila |
| 5,562,633 A | 10/1996 | Wozencroft |
| 5,562,636 A | 10/1996 | Utterberg |
| 5,562,637 A | 10/1996 | Utterberg |
| 5,569,202 A | 10/1996 | Kovalic |
| 5,569,203 A | 10/1996 | Chen |
| 5,569,205 A | 10/1996 | Hart |
| 5,569,209 A | 10/1996 | Roitman |
| 5,569,288 A | 10/1996 | Yoon |
| 5,573,545 A | 11/1996 | Yoon |
| 5,575,774 A | 11/1996 | Chen |
| 5,575,777 A | 11/1996 | Davidner et al. |
| 5,575,804 A | 11/1996 | Yoon |
| 5,578,059 A | 11/1996 | Patzer |
| 5,582,594 A | 12/1996 | Chen |
| 5,582,597 A | 12/1996 | Brimhall |
| 5,584,808 A | 12/1996 | Healy |
| 5,584,809 A | 12/1996 | Gaba |
| 5,584,810 A | 12/1996 | Brimhall |
| 5,584,818 A | 12/1996 | Morrison |
| 5,584,848 A | 12/1996 | Yoon |
| 5,584,849 A | 12/1996 | Yoon |
| 5,584,850 A | 12/1996 | Hart |
| 5,588,966 A | 12/1996 | Atsumi |
| 5,591,134 A | 1/1997 | Shu |
| 5,591,137 A | 1/1997 | Stevens |
| 5,591,190 A | 1/1997 | Yoon |
| 5,591,193 A | 1/1997 | Yoon |
| 5,599,310 A | 2/1997 | Bogert |
| 5,601,532 A | 2/1997 | Gaba |
| 5,601,534 A | 2/1997 | Turner |
| 5,601,536 A | 2/1997 | Crawford |
| 5,607,396 A | 3/1997 | Yoon |
| 5,607,439 A | 3/1997 | Yoon |
| 5,611,781 A | 3/1997 | Sircom |
| 5,611,792 A | 3/1997 | Gustafsson |
| 5,613,500 A | 3/1997 | Bishop |
| 5,613,663 A | 3/1997 | Schmidt |
| 5,613,952 A | 3/1997 | Pressly, Sr. |
| 5,613,954 A | 3/1997 | Nelson |
| 5,613,956 A | 3/1997 | Patterson |
| 5,616,129 A | 4/1997 | Mayer |
| 5,616,130 A | 4/1997 | Mayer |
| 5,618,271 A | 4/1997 | Yoon |
| 5,630,803 A | 5/1997 | Tamaro |
| 5,634,913 A | 6/1997 | Stinger |
| 5,634,934 A | 6/1997 | Yoon |
| 5,643,227 A | 7/1997 | Stevens |

(56) References Cited

U.S. PATENT DOCUMENTS

| | | |
|---|---|---|
| 5,645,076 A | 7/1997 | Yoon |
| 5,645,533 A | 7/1997 | Blaeser |
| 5,651,772 A | 7/1997 | Arnett |
| 5,653,698 A | 8/1997 | Niedospial |
| 5,662,610 A | 9/1997 | Sircom |
| 5,669,891 A | 9/1997 | Vaillancourt |
| 5,672,160 A | 9/1997 | Osterlind |
| 5,672,161 A | 9/1997 | Allen |
| 5,676,681 A | 10/1997 | Yoon |
| 5,676,682 A | 10/1997 | Yoon |
| 5,676,683 A | 10/1997 | Yoon |
| 5,683,365 A | 11/1997 | Brown |
| 5,683,368 A | 11/1997 | Schmidt |
| 5,685,855 A | 11/1997 | Erskine |
| 5,685,860 A | 11/1997 | Chang |
| 5,688,240 A | 11/1997 | Novacek |
| 5,688,253 A | 11/1997 | Paradis |
| 5,688,254 A | 11/1997 | Lopez |
| 5,688,286 A | 11/1997 | Yoon |
| 5,693,025 A | 12/1997 | Stevens |
| 5,693,031 A | 12/1997 | Ryan |
| 5,695,474 A | 12/1997 | Daugherty |
| 5,696,466 A | 12/1997 | Li |
| 5,697,907 A | 12/1997 | Gaba |
| 5,699,821 A | 12/1997 | Paradis |
| 5,700,249 A | 12/1997 | Jenkins |
| 5,700,250 A | 12/1997 | Erskine |
| 5,702,367 A | 12/1997 | Cover |
| 5,709,664 A | 1/1998 | Vandenbroek |
| 5,718,688 A | 2/1998 | Wozencroft |
| 5,718,689 A | 2/1998 | Stevenson |
| 5,718,691 A | 2/1998 | Russo |
| 5,720,734 A | 2/1998 | Copenhaver |
| 5,722,958 A | 3/1998 | Gravener |
| 5,725,503 A | 3/1998 | Arnett |
| 5,735,827 A | 4/1998 | Adwers |
| 5,738,144 A | 4/1998 | Rogers |
| 5,738,665 A | 4/1998 | Caizza |
| 5,743,884 A | 4/1998 | Hasson |
| 5,743,888 A | 4/1998 | Wilkes |
| 5,743,891 A | 4/1998 | Tolkoff et al. |
| 5,746,718 A | 5/1998 | Steyn |
| 5,749,857 A | 5/1998 | Cuppy |
| 5,749,859 A | 5/1998 | Powell |
| 5,749,861 A | 5/1998 | Guala |
| 5,749,889 A | 5/1998 | Bacich |
| 5,755,699 A | 5/1998 | Blecher |
| 5,755,701 A | 5/1998 | Sarstedt |
| 5,772,636 A | 6/1998 | Brimhall |
| 5,776,113 A | 7/1998 | Daugherty |
| 5,779,681 A | 7/1998 | Bonn |
| 5,779,684 A | 7/1998 | Tamaro |
| 5,782,804 A | 7/1998 | Mcmahon |
| D397,434 S | 8/1998 | Pike |
| 5,788,675 A | 8/1998 | Mayer |
| 5,792,121 A | 8/1998 | Tamaro |
| 5,795,339 A | 8/1998 | Erskine |
| 5,797,897 A | 8/1998 | Jepson |
| 5,800,403 A | 9/1998 | Pressly, Sr. |
| 5,803,919 A | 9/1998 | Hart |
| 5,806,831 A | 9/1998 | Paradis |
| 5,807,350 A | 9/1998 | Diaz |
| 5,807,352 A | 9/1998 | Tamaro |
| 5,807,353 A | 9/1998 | Schmitz |
| 5,810,784 A | 9/1998 | Tamaro |
| 5,814,018 A | 9/1998 | Elson |
| 5,817,069 A | 10/1998 | Arnett |
| 5,817,070 A | 10/1998 | Tamaro |
| 5,820,606 A | 10/1998 | Davis |
| 5,820,614 A | 10/1998 | Erskine |
| 5,820,621 A | 10/1998 | Yale |
| 5,830,189 A | 11/1998 | Chang |
| 5,833,670 A | 11/1998 | Dillon |
| 5,851,196 A | 12/1998 | Arnett |
| 5,853,393 A | 12/1998 | Bogert |
| 5,853,399 A | 12/1998 | Sasaki |
| 5,857,999 A | 1/1999 | Quick |
| 5,858,000 A | 1/1999 | Novacek |
| 5,858,007 A | 1/1999 | Fagan |
| 5,865,806 A | 2/1999 | Howell |
| 5,871,471 A | 2/1999 | Ryan |
| 5,879,331 A | 3/1999 | Osterlind |
| 5,879,337 A | 3/1999 | Kuracina |
| 5,882,337 A | 3/1999 | Boger |
| 5,885,256 A | 3/1999 | Chern et al. |
| 5,891,093 A | 4/1999 | Dysarz |
| 5,899,887 A | 5/1999 | Liu |
| 5,910,130 A | 6/1999 | Caizza |
| 5,911,705 A | 6/1999 | Howell |
| 5,911,710 A | 6/1999 | Barry |
| 5,916,198 A | 6/1999 | Dillow |
| 5,919,168 A | 7/1999 | Wheeler |
| 5,919,174 A | 7/1999 | Hanson |
| 5,925,020 A | 7/1999 | Nestell |
| 5,935,104 A | 8/1999 | Janek |
| 5,941,850 A | 8/1999 | Shah |
| 5,951,515 A | 9/1999 | Osterlind |
| 5,951,529 A | 9/1999 | Utterberg |
| 5,954,698 A | 9/1999 | Pike |
| 5,954,708 A | 9/1999 | Lopez |
| 5,957,887 A | 9/1999 | Osterlind |
| 5,957,898 A | 9/1999 | Jepson |
| 5,967,490 A | 10/1999 | Pike |
| 5,968,068 A | 10/1999 | Dehdashtian |
| 5,971,957 A | 10/1999 | Luther |
| 5,989,224 A | 11/1999 | Exline |
| 5,993,419 A | 11/1999 | Lo |
| 5,997,486 A | 12/1999 | Burek |
| 5,997,507 A | 12/1999 | Dysarz |
| 6,001,080 A | 12/1999 | Kuracina |
| 6,004,294 A | 12/1999 | Brimhall |
| 6,012,213 A | 1/2000 | Chang |
| 6,015,397 A | 1/2000 | Elson |
| 6,024,729 A | 2/2000 | Dehdashtian |
| 6,033,386 A | 3/2000 | Novacek |
| 6,036,672 A | 3/2000 | Allen |
| 6,039,302 A | 3/2000 | Cote, Sr. |
| 6,048,335 A | 4/2000 | Mayer |
| 6,053,861 A | 4/2000 | Grossi |
| 6,068,011 A | 5/2000 | Paradis |
| 6,074,370 A | 6/2000 | Pressly, Jr. |
| 6,077,244 A | 6/2000 | Botich |
| 6,079,432 A | 6/2000 | Paradis |
| 6,080,135 A | 6/2000 | Van Stokkum |
| 6,080,137 A | 6/2000 | Pike |
| 6,086,566 A | 7/2000 | Arnissolle |
| 6,099,500 A | 8/2000 | Dysarz |
| 6,099,505 A | 8/2000 | Ryan |
| 6,102,894 A | 8/2000 | Dysarz |
| RE36,885 E | 9/2000 | Blecher |
| 6,117,107 A | 9/2000 | Chen |
| 6,117,108 A | 9/2000 | Woehr |
| 6,117,110 A | 9/2000 | Radmand |
| 6,117,113 A | 9/2000 | Novacek |
| 6,127,320 A | 10/2000 | Ooij |
| 6,152,900 A | 11/2000 | Mayer |
| 6,156,010 A | 12/2000 | Kuracina |
| 6,159,185 A | 12/2000 | Tanihata |
| 6,162,196 A | 12/2000 | Hart |
| 6,171,287 B1 | 1/2001 | Lynn |
| 6,183,440 B1 | 2/2001 | Bell |
| 6,183,448 B1 | 2/2001 | Mayer |
| 6,193,690 B1 | 2/2001 | Dysarz |
| 6,200,262 B1 | 3/2001 | Ouchi |
| 6,203,527 B1 | 3/2001 | Zadini |
| 6,203,533 B1 | 3/2001 | Ouchi |
| 6,206,857 B1 | 3/2001 | Chen |
| 6,210,373 B1 | 4/2001 | Allmon |
| 6,213,978 B1 | 4/2001 | Voyten |
| 6,217,555 B1 | 4/2001 | Hart |
| 6,217,568 B1 | 4/2001 | Jepson |
| 6,221,047 B1 | 4/2001 | Greene |
| 6,221,050 B1 | 4/2001 | Ishida |
| 6,221,056 B1 | 4/2001 | Silverman |

(56) References Cited

U.S. PATENT DOCUMENTS

| | | |
|---|---|---|
| 6,224,569 B1 | 5/2001 | Brimhall |
| 6,228,060 B1 | 5/2001 | Howell |
| 6,234,999 B1 | 5/2001 | Wemmert |
| 6,235,003 B1 | 5/2001 | Dysarz |
| 6,235,006 B1 | 5/2001 | Dillon |
| 6,241,707 B1 | 6/2001 | Dysarz |
| 6,245,045 B1 | 6/2001 | Stratienko |
| 6,245,048 B1 | 6/2001 | Fangrow |
| 6,254,529 B1 | 7/2001 | Ouchi |
| 6,258,065 B1 | 7/2001 | Dennis |
| 6,261,264 B1 | 7/2001 | Tamaro |
| 6,261,265 B1 | 7/2001 | Mosseri |
| 6,273,869 B1 | 8/2001 | Vaillancourt |
| 6,277,100 B1 | 8/2001 | Raulerson |
| 6,280,419 B1 | 8/2001 | Vojtasek |
| 6,287,278 B1 | 9/2001 | Woehr |
| 6,287,279 B1 | 9/2001 | Siekmann |
| 6,287,280 B1 | 9/2001 | Lampropoulos |
| 6,306,124 B1 | 10/2001 | Jones |
| 6,322,537 B1 | 11/2001 | Chang |
| 6,322,541 B2 | 11/2001 | West |
| 6,342,045 B1 | 1/2002 | Somers |
| 6,344,031 B1 | 2/2002 | Novacek |
| 6,344,033 B1 | 2/2002 | Jepson |
| 6,352,520 B1 | 3/2002 | Miyazaki |
| 6,352,521 B1 | 3/2002 | Prosl |
| 6,358,265 B1 | 3/2002 | Thorne, Jr. |
| 6,379,332 B1 | 4/2002 | Van Landuyt |
| 6,379,333 B1 | 4/2002 | Brimhall |
| 6,379,372 B1 | 4/2002 | Dehdashtian |
| 6,394,983 B1 | 5/2002 | Mayoral |
| 6,402,721 B1 | 6/2002 | Lo |
| 6,406,459 B1 | 6/2002 | Allmon |
| 6,409,703 B1 | 6/2002 | Lu |
| 6,413,236 B1 | 7/2002 | Van Dyke |
| 6,416,499 B2 | 7/2002 | Paul, Jr. |
| 6,425,884 B1 | 7/2002 | Wemmert |
| 6,440,101 B1 | 8/2002 | Grabenkort |
| 6,443,927 B1 | 9/2002 | Cook |
| 6,443,929 B1 | 9/2002 | Kuracina |
| 6,461,328 B2 | 10/2002 | Wang |
| 6,475,194 B2 | 11/2002 | Domici, Jr. |
| 6,485,459 B1 | 11/2002 | Surowitz |
| 6,485,468 B2 | 11/2002 | Vojtasek |
| 6,488,656 B1 | 12/2002 | Wu |
| 6,488,663 B1 | 12/2002 | Steg |
| 6,488,674 B2 | 12/2002 | Becker |
| 6,506,181 B2 | 1/2003 | Meng |
| 6,520,939 B2 | 2/2003 | Lafontaine |
| 6,524,276 B1 | 2/2003 | Halseth |
| 6,524,278 B1 | 2/2003 | Campbell |
| 6,527,747 B2 | 3/2003 | Adams |
| 6,530,903 B2 | 3/2003 | Wang |
| 6,533,759 B1 | 3/2003 | Watson |
| 6,537,259 B1 | 3/2003 | Niermann |
| 6,545,242 B1 | 4/2003 | Butler |
| 6,551,283 B1 | 4/2003 | Guo |
| 6,569,119 B1 | 5/2003 | Haberland |
| 6,572,591 B2 | 6/2003 | Mayer |
| 6,582,402 B1 | 6/2003 | Erskine |
| 6,585,701 B1 | 7/2003 | Dysarz |
| 6,585,704 B2 | 7/2003 | Luther |
| 6,592,555 B1 | 7/2003 | Pi |
| 6,592,556 B1 | 7/2003 | Thorne |
| 6,595,954 B1 | 7/2003 | Luther |
| 6,595,955 B2 | 7/2003 | Ferguson |
| 6,595,964 B2 | 7/2003 | Finley |
| 6,595,965 B2 | 7/2003 | Utterberg |
| 6,595,981 B2 | 7/2003 | Huet |
| 6,602,240 B2 | 8/2003 | Hermann |
| 6,605,073 B1 | 8/2003 | Pressly, Sr. |
| 6,610,031 B1 | 8/2003 | Chin |
| 6,616,630 B1 | 9/2003 | Woehr |
| 6,616,640 B2 | 9/2003 | Chen |
| 6,620,136 B1 | 9/2003 | Pressly, Sr |
| 6,623,458 B2 | 9/2003 | Woehr |
| 6,629,959 B2 | 10/2003 | Kuracina |
| 6,632,200 B2 | 10/2003 | Guo |
| 6,632,201 B1 | 10/2003 | Mathias |
| 6,641,564 B1 | 11/2003 | Kraus |
| 6,651,956 B2 | 11/2003 | Miller |
| 6,652,486 B2 | 11/2003 | Bialecki |
| 6,652,490 B2 | 11/2003 | Howell |
| 6,663,592 B2 | 12/2003 | Rhad |
| 6,663,599 B2 | 12/2003 | Osbourne |
| 6,669,666 B2 | 12/2003 | Lu |
| 6,669,681 B2 | 12/2003 | Jepson |
| 6,682,510 B2 | 1/2004 | Niermann |
| 6,689,102 B2 | 2/2004 | Greene |
| 6,692,471 B2 | 2/2004 | Boudreaux |
| 6,695,814 B2 | 2/2004 | Greene |
| 6,695,817 B1 | 2/2004 | Fangrow, Jr. |
| 6,699,221 B2 | 3/2004 | Vaillancourt |
| 6,706,022 B1 | 3/2004 | Leinsing |
| 6,709,419 B2 | 3/2004 | Woehr |
| 6,712,791 B2 | 3/2004 | Lui |
| 6,719,726 B2 | 4/2004 | Meng |
| 6,723,073 B2 | 4/2004 | Ley |
| 6,736,798 B2 | 5/2004 | Ohkubo |
| 6,743,199 B2 | 6/2004 | Shue |
| 6,749,588 B1 | 6/2004 | Howell |
| 6,761,704 B2 | 7/2004 | Crawford |
| 6,761,705 B1 | 7/2004 | Chiu |
| 6,761,706 B2 | 7/2004 | Vaillancourt |
| 6,764,468 B1 | 7/2004 | East |
| 6,767,340 B2 | 7/2004 | Willis |
| 6,770,059 B1 | 8/2004 | Spinks |
| 6,773,416 B1 | 8/2004 | Hsu |
| 6,776,774 B2 | 8/2004 | Tansey, Jr. |
| 6,796,962 B2 | 9/2004 | Ferguson |
| 6,796,968 B2 | 9/2004 | Ferguson |
| 6,796,969 B1 | 9/2004 | Andersson |
| 6,802,827 B2 | 10/2004 | Andersson |
| 6,808,161 B1 | 10/2004 | Hishikawa |
| 6,808,509 B1 | 10/2004 | Davey |
| 6,811,545 B2 | 11/2004 | Vaillancourt |
| 6,817,989 B2 | 11/2004 | Svendsen |
| 6,821,266 B2 | 11/2004 | Knepshield |
| 6,824,527 B2 | 11/2004 | Gollobin |
| 6,832,992 B2 | 12/2004 | Wilkinson |
| 6,855,127 B2 | 2/2005 | Nakagami |
| 6,855,130 B2 | 2/2005 | Saulenas |
| 6,860,869 B2 | 3/2005 | Dennis |
| 6,860,871 B2 | 3/2005 | Kuracina |
| 6,863,659 B2 | 3/2005 | Sharpe |
| 6,866,656 B2 | 3/2005 | Tingey |
| 6,878,131 B2 | 4/2005 | Novacek |
| 6,878,134 B2 | 4/2005 | Rogers |
| 6,883,778 B1 | 4/2005 | Newton |
| 6,884,224 B2 | 4/2005 | Dalton |
| 6,886,808 B2 | 5/2005 | Sarno |
| 6,893,423 B2 | 5/2005 | Denolly |
| 6,902,546 B2 | 6/2005 | Ferguson |
| 6,905,483 B2 | 6/2005 | Newby |
| 6,908,459 B2 | 6/2005 | Harding |
| 6,911,018 B2 | 6/2005 | Gordon |
| 6,913,595 B2 | 7/2005 | Mastorakis |
| 6,916,309 B2 | 7/2005 | Fangrow, Jr. |
| 6,916,311 B2 | 7/2005 | Vojtasek |
| 6,918,891 B2 | 7/2005 | Bressler |
| 6,921,382 B2 | 7/2005 | Lee |
| 6,921,386 B2 | 7/2005 | Shue |
| 6,926,698 B2 | 8/2005 | Lin |
| 6,926,700 B2 | 8/2005 | Bressler |
| 6,929,622 B2 | 8/2005 | Chian |
| 6,932,803 B2 | 8/2005 | Newby |
| 6,936,031 B2 | 8/2005 | Caleffi |
| 6,936,036 B2 | 8/2005 | Wilkinson |
| 6,942,642 B2 | 9/2005 | Suzuki |
| 6,958,055 B2 | 10/2005 | Donnan |
| 6,972,002 B2 | 12/2005 | Thorne |
| 6,979,314 B2 | 12/2005 | Hsieh |
| 6,981,965 B2 | 1/2006 | Luther |
| 6,984,213 B2 | 1/2006 | Horner |

(56) References Cited

U.S. PATENT DOCUMENTS

| | | |
|---|---|---|
| 6,986,759 B1 | 1/2006 | Jeremijevic |
| 6,991,215 B2 | 1/2006 | Kiehne |
| RE38,996 E | 2/2006 | Crawford |
| 6,997,902 B2 | 2/2006 | Thorne |
| 7,004,927 B2 | 2/2006 | Ferguson |
| 7,004,934 B2 | 2/2006 | Vaillancourt |
| 7,008,402 B2 | 3/2006 | Ferguson |
| 7,008,404 B2 | 3/2006 | Nakajima |
| 7,014,623 B2 | 3/2006 | Prestidge |
| 7,018,344 B2 | 3/2006 | Bressler |
| 7,018,365 B2 | 3/2006 | Strauss |
| 7,025,721 B2 | 4/2006 | Cohen |
| 7,025,744 B2 | 4/2006 | Utterberg |
| 7,033,339 B1 | 4/2006 | Lynn |
| 7,033,345 B2 | 4/2006 | Lee |
| 7,037,292 B2 | 5/2006 | Carlyon |
| 7,037,303 B2 | 5/2006 | Beaufore |
| 7,060,053 B2 | 6/2006 | Nakashima |
| 7,063,685 B2 | 6/2006 | Rome |
| 7,066,908 B2 | 6/2006 | Kuracina |
| 7,077,824 B2 | 7/2006 | Meyer |
| 7,081,106 B1 | 7/2006 | Guo |
| 7,083,596 B2 | 8/2006 | Saied |
| 7,083,600 B2 | 8/2006 | Meloul |
| 7,101,351 B2 | 9/2006 | Crawford |
| 7,101,353 B2 | 9/2006 | Lui |
| 7,104,970 B2 | 9/2006 | Chen |
| 7,112,191 B2 | 9/2006 | Daga |
| 7,125,396 B2 | 10/2006 | Leinsing |
| 7,125,397 B2 | 10/2006 | Woehr |
| 7,147,621 B2 | 12/2006 | Kiehne |
| 7,150,725 B2 | 12/2006 | Wilkinson |
| 7,160,269 B2 | 1/2007 | Woehr |
| 7,172,580 B2 | 2/2007 | Hruska |
| 7,175,610 B2 | 2/2007 | Mori |
| 7,179,244 B2 | 2/2007 | Smith |
| 7,182,734 B2 | 2/2007 | Saulenas |
| 7,186,239 B2 | 3/2007 | Woehr |
| 7,192,433 B2 | 3/2007 | Osypk |
| 7,198,618 B2 | 4/2007 | Ferguson |
| 7,207,975 B2 | 4/2007 | Miller |
| 7,214,208 B2 | 5/2007 | Vaillancourt |
| 7,214,211 B2 | 5/2007 | Woehr |
| 7,226,434 B2 | 6/2007 | Carlyon |
| 7,235,062 B2 | 6/2007 | Brustad |
| 7,238,169 B2 | 7/2007 | Takagi |
| 7,239,169 B2 | 7/2007 | Isa |
| 7,247,148 B2 | 7/2007 | Murashita |
| 7,252,651 B2 | 8/2007 | Haider |
| 7,264,613 B2 | 9/2007 | Woehr |
| 7,291,128 B2 | 11/2007 | Rossi |
| 7,291,130 B2 | 11/2007 | McGurk |
| 7,297,138 B2 | 11/2007 | Fangrow, Jr. |
| 7,300,419 B2 | 11/2007 | Fangrow, Jr. |
| 7,303,548 B2 | 12/2007 | Rhad |
| 7,306,579 B2 | 12/2007 | Fujii |
| 7,309,326 B2 | 12/2007 | Fangrow, Jr. |
| 7,311,693 B2 | 12/2007 | Shekalim |
| 7,311,694 B2 | 12/2007 | Fangrow, Jr. |
| 7,314,462 B2 | 1/2008 | O'Reagan |
| 7,314,463 B2 | 1/2008 | Fangrow, Jr. |
| 7,316,667 B2 | 1/2008 | Lindstrom |
| 7,318,818 B2 | 1/2008 | Yashiro |
| 7,326,189 B2 | 2/2008 | Mori |
| 7,331,934 B2 | 2/2008 | Suresh |
| 7,331,935 B2 | 2/2008 | Barere |
| 7,331,939 B2 | 2/2008 | Fangrow, Jr. |
| 7,341,573 B2 | 3/2008 | Ferguson |
| 7,347,838 B2 | 3/2008 | Kulli |
| 7,347,839 B2 | 3/2008 | Hiejima |
| 7,347,842 B2 | 3/2008 | Thorne |
| 7,354,422 B2 | 4/2008 | Riesenberger |
| 7,357,784 B2 | 4/2008 | Ferguson |
| 7,361,164 B2 | 4/2008 | Simpson |
| 7,371,226 B2 | 5/2008 | Huang |
| 7,371,227 B2 | 5/2008 | Zeiner |
| 7,374,554 B2 | 5/2008 | Menzi |
| 7,387,616 B2 | 6/2008 | Li |
| 7,396,346 B2 | 7/2008 | Nakajima |
| 7,399,293 B2 | 7/2008 | Oyibo |
| 7,407,491 B2 | 8/2008 | Fangrow, Jr. |
| 7,407,495 B2 | 8/2008 | Barere |
| 7,413,562 B2 | 8/2008 | Ferguson |
| 7,422,571 B2 | 9/2008 | Schweikert |
| 7,422,573 B2 | 9/2008 | Wilkinson |
| 7,445,611 B2 | 11/2008 | Osborne |
| 7,458,954 B2 | 12/2008 | Ferguson |
| 7,470,254 B2 | 12/2008 | Basta |
| 7,470,261 B2 | 12/2008 | Lynn |
| 7,470,262 B2 | 12/2008 | Hiejima |
| 7,497,847 B2 | 3/2009 | Crawford |
| 7,497,849 B2 | 3/2009 | Fangrow, Jr. |
| 7,500,965 B2 | 3/2009 | Menzi |
| 7,507,222 B2 | 3/2009 | Cindrich |
| 7,513,887 B2 | 4/2009 | Halseth |
| 7,513,888 B2 | 4/2009 | Sircom et al. |
| 7,524,300 B2 | 4/2009 | Patton |
| 7,530,965 B2 | 5/2009 | Villa |
| 7,534,227 B2 | 5/2009 | Kulli |
| 7,534,231 B2 | 5/2009 | Kuracina |
| 7,537,582 B2 | 5/2009 | Suresh |
| 7,544,181 B2 | 6/2009 | Axelsson |
| 7,566,323 B2 | 7/2009 | Chang |
| 7,566,327 B2 | 7/2009 | Mathias |
| 7,569,033 B2 | 8/2009 | Greene |
| 7,572,247 B2 | 8/2009 | Smith |
| 7,575,570 B2 | 8/2009 | Barere |
| 7,578,803 B2 | 8/2009 | Rome |
| 7,578,805 B2 | 8/2009 | Hwang |
| 7,578,806 B2 | 8/2009 | Zeoli |
| 7,591,449 B2 | 9/2009 | Raines |
| 7,597,681 B2 | 10/2009 | Sutton |
| 7,597,684 B2 | 10/2009 | Alchas |
| 7,601,139 B2 | 10/2009 | Woehr |
| 7,604,616 B2 | 10/2009 | Thoresen |
| 7,608,057 B2 | 10/2009 | Woehr |
| 7,611,485 B2 | 11/2009 | Ferguson |
| 7,611,487 B2 | 11/2009 | Woehr |
| 7,611,488 B2 | 11/2009 | Chang |
| 7,611,499 B2 | 11/2009 | Woehr |
| 7,614,423 B2 | 11/2009 | Yokota |
| 7,618,395 B2 | 11/2009 | Ferguson |
| 7,625,360 B2 | 12/2009 | Woehr |
| 7,628,774 B2 | 12/2009 | Fangrow, Jr. |
| 7,628,776 B2 | 12/2009 | Gibson |
| 7,632,243 B2 | 12/2009 | Bialecki |
| 7,635,352 B2 | 12/2009 | Adams |
| 7,635,357 B2 | 12/2009 | Mayer |
| 7,637,887 B2 | 12/2009 | Woehr |
| 7,637,888 B2 | 12/2009 | Schwarzich |
| 7,637,893 B2 | 12/2009 | Christensen |
| 7,651,476 B2 | 1/2010 | Kohler |
| 7,651,481 B2 | 1/2010 | Raybuck |
| 7,654,988 B2 | 2/2010 | Moulton |
| 7,658,725 B2 | 2/2010 | Bialecki |
| 7,662,134 B2 | 2/2010 | Miller |
| 7,666,170 B2 | 2/2010 | Guala |
| 7,670,317 B2 | 3/2010 | Cindrich |
| 7,670,320 B2 | 3/2010 | Iwase |
| 7,682,331 B2 | 3/2010 | Carrez |
| 7,682,339 B2 | 3/2010 | Fujii |
| 7,682,340 B2 | 3/2010 | Funamura |
| 7,686,784 B2 | 3/2010 | Baik |
| 7,691,088 B2 | 4/2010 | Howell |
| 7,694,403 B2 | 4/2010 | Moulton |
| 7,713,242 B2 | 5/2010 | Streifinger |
| 7,713,243 B2 | 5/2010 | Hillman |
| 7,713,250 B2 | 5/2010 | Harding |
| 7,713,256 B2 | 5/2010 | Brimhall |
| 7,713,257 B2 | 5/2010 | Brimhall |
| 7,717,888 B2 | 5/2010 | Vaillancourt |
| 7,722,563 B2 | 5/2010 | Isaacson |
| 7,722,564 B2 | 5/2010 | Vaillancourt |
| 7,722,569 B2 | 5/2010 | Soderholm |

(56) References Cited

U.S. PATENT DOCUMENTS

| | | |
|---|---|---|
| 7,727,198 B2 | 6/2010 | Nakajima |
| 7,731,687 B2 | 6/2010 | Menzi |
| 7,731,694 B2 | 6/2010 | Becker |
| 7,736,332 B2 | 6/2010 | Carlyon |
| 7,736,337 B2 | 6/2010 | Diep |
| 7,736,339 B2 | 6/2010 | Woehr |
| 7,736,340 B2 | 6/2010 | Harding |
| 7,736,342 B2 | 6/2010 | Abriles |
| 7,740,613 B2 | 6/2010 | Yokoi |
| 7,740,614 B2 | 6/2010 | Murashita |
| 7,744,567 B2 | 6/2010 | Glowacki |
| 7,744,568 B2 | 6/2010 | Douglas |
| 7,744,570 B2 | 6/2010 | Fangrow, Jr. |
| 7,753,338 B2 | 7/2010 | Desecki |
| 7,753,877 B2 | 7/2010 | Bialecki |
| 7,753,887 B2 | 7/2010 | Botich |
| 7,758,543 B2 | 7/2010 | Ferraresi |
| 7,762,986 B2 | 7/2010 | Wang |
| 7,763,199 B2 | 7/2010 | Fangrow, Jr. |
| 7,771,412 B2 | 8/2010 | Anderson |
| 7,785,296 B2 | 8/2010 | Muskatello |
| 7,794,445 B2 | 9/2010 | Dalton |
| 7,794,675 B2 | 9/2010 | Lynn |
| 7,798,994 B2 | 9/2010 | Brimhall |
| 7,806,849 B2 | 10/2010 | Woehr |
| 7,806,858 B2 | 10/2010 | Smith |
| 7,806,869 B2 | 10/2010 | Nilsson |
| 7,806,890 B2 | 10/2010 | McKinnon |
| 7,811,261 B2 | 10/2010 | Rubinstein |
| 7,815,614 B2 | 10/2010 | Fangrow, Jr. |
| 7,824,393 B2 | 11/2010 | Fangrow |
| 7,828,773 B2 | 11/2010 | Swisher |
| 7,828,774 B2 | 11/2010 | Harding |
| 7,833,199 B2 | 11/2010 | Franer |
| 7,850,648 B2 | 12/2010 | Gratwohl |
| 7,850,650 B2 | 12/2010 | Breitweiser |
| 7,850,652 B2 | 12/2010 | Liniger |
| 7,867,204 B2 | 1/2011 | Bartholomew |
| 7,887,516 B2 | 2/2011 | Young |
| 7,892,209 B2 | 2/2011 | Harand |
| 7,892,216 B2 | 2/2011 | Fangrow, Jr. |
| 7,901,379 B2 | 3/2011 | Argentine |
| 7,905,857 B2 | 3/2011 | Swisher |
| 7,914,488 B2 | 3/2011 | Dickerson |
| 7,914,494 B2 | 3/2011 | Hiejima |
| 7,914,519 B2 | 3/2011 | Moran |
| 7,922,698 B2 | 4/2011 | Riesenberger |
| 7,927,314 B2 | 4/2011 | Kuracina |
| 7,931,615 B2 | 4/2011 | Fangrow, Jr. |
| 7,931,622 B2 | 4/2011 | Beling |
| 7,935,080 B2 | 5/2011 | Howell |
| 7,935,090 B2 | 5/2011 | Patton |
| 7,938,805 B2 | 5/2011 | Harding |
| 7,947,018 B2 | 5/2011 | Mckinnon |
| 7,947,032 B2 | 5/2011 | Harding |
| 7,951,119 B2 | 5/2011 | Leeflang |
| 7,951,122 B2 | 5/2011 | Shekalim |
| 7,955,306 B2 | 6/2011 | Wyss |
| 7,959,613 B2 | 6/2011 | Rhad |
| 7,967,797 B2 | 6/2011 | Winsor |
| 7,972,300 B2 | 7/2011 | Smith |
| 7,972,313 B2 | 7/2011 | Woehr |
| 7,976,498 B2 | 7/2011 | Swisher |
| 7,976,502 B2 | 7/2011 | Baid |
| 7,976,503 B2 | 7/2011 | Khan |
| 7,981,090 B2 | 7/2011 | Plishka |
| 7,985,199 B2 | 7/2011 | Kornerup |
| 7,985,232 B2 | 7/2011 | Potter |
| 7,988,664 B2 | 8/2011 | Fiser |
| 7,993,305 B2 | 8/2011 | Ye |
| 7,993,306 B2 | 8/2011 | Marrs |
| 7,998,122 B2 | 8/2011 | Lynn |
| 8,002,765 B2 | 8/2011 | Lopez |
| 8,006,953 B2 | 8/2011 | Bennett |
| 8,016,791 B2 | 9/2011 | Sugiki |
| 8,021,343 B2 | 9/2011 | Nalesso |
| 8,025,646 B2 | 9/2011 | Fukai |
| 8,029,472 B2 | 10/2011 | Leinsing |
| 8,038,647 B2 | 10/2011 | Harding |
| 8,043,263 B2 | 10/2011 | Helgeson |
| 8,043,266 B2 | 10/2011 | Murashita |
| 8,043,316 B2 | 10/2011 | Hardin |
| 8,048,031 B2 | 11/2011 | Shaw |
| 8,048,039 B2 | 11/2011 | Carlyon |
| 8,052,646 B2 | 11/2011 | Schweikert |
| 8,052,647 B2 | 11/2011 | Raulerson |
| 8,052,653 B2 | 11/2011 | Gratwohl |
| 8,062,261 B2 | 11/2011 | Adams |
| 8,066,670 B2 | 11/2011 | Cluff |
| 8,075,529 B2 | 12/2011 | Nakajima |
| RE43,141 E | 1/2012 | Halseth |
| 8,088,104 B2 | 1/2012 | Smith |
| 8,096,973 B2 | 1/2012 | Snow |
| 8,100,857 B2 | 1/2012 | Kuracina |
| 8,100,858 B2 | 1/2012 | Woehr |
| 8,105,276 B2 | 1/2012 | Chen |
| 8,123,738 B2 | 2/2012 | Vaillancourt |
| 8,128,594 B1 | 3/2012 | Chang |
| 8,133,207 B2 | 3/2012 | Wilkinson |
| 8,133,209 B2 | 3/2012 | Guala |
| 8,137,321 B2 | 3/2012 | Argentine |
| 8,147,455 B2 | 4/2012 | Butts |
| 8,157,768 B2 | 4/2012 | Haider |
| 8,162,881 B2 | 4/2012 | Lilley, Jr. |
| 8,162,889 B2 | 4/2012 | Swisher |
| 8,162,904 B2 | 4/2012 | Takano |
| 8,197,452 B2 | 6/2012 | Harding |
| 8,206,355 B2 | 6/2012 | Thorne |
| 8,211,070 B2 | 7/2012 | Woehr |
| 8,226,627 B2 | 7/2012 | Fowles |
| 8,231,525 B2 | 7/2012 | Cohen |
| 8,251,950 B2 | 8/2012 | Albert |
| 8,257,322 B2 | 9/2012 | Koehler |
| 2001/0021821 A1 | 9/2001 | Wang |
| 2001/0021827 A1 | 9/2001 | Ferguson |
| 2001/0039401 A1 | 11/2001 | Ferguson |
| 2002/0010434 A1 | 1/2002 | Larsen |
| 2002/0022803 A1 | 2/2002 | Wemmert |
| 2002/0026154 A1 | 2/2002 | Chang |
| 2002/0065488 A1 | 5/2002 | Suzuki |
| 2002/0065489 A1 | 5/2002 | Novacek |
| 2002/0128604 A1 | 9/2002 | Nakajima |
| 2002/0151850 A1 | 10/2002 | Ferguson |
| 2002/0156428 A1 | 10/2002 | Lee |
| 2003/0060785 A1 | 3/2003 | Lavean |
| 2003/0105431 A1 | 6/2003 | Howell |
| 2003/0114797 A1 | 6/2003 | Vaillancourt |
| 2003/0125676 A1 | 7/2003 | Swenson |
| 2003/0125677 A1 | 7/2003 | Swenson |
| 2003/0130623 A1 | 7/2003 | Chen |
| 2003/0144627 A1 | 7/2003 | Woehr |
| 2003/0181867 A1 | 9/2003 | Bressler |
| 2003/0181869 A1 | 9/2003 | Swenson |
| 2003/0181870 A1 | 9/2003 | Bressler |
| 2003/0181871 A1 | 9/2003 | Wilkinson |
| 2003/0181875 A1 | 9/2003 | Bressler |
| 2003/0195471 A1 | 10/2003 | Woehr |
| 2003/0195479 A1 | 10/2003 | Kuracina |
| 2003/0199827 A1 | 10/2003 | Thorne |
| 2003/0216687 A1 | 11/2003 | Hwang |
| 2003/0229316 A1 | 12/2003 | Hwang |
| 2004/0006313 A1 | 1/2004 | Chian |
| 2004/0019334 A1 | 1/2004 | Ohkubo |
| 2004/0039333 A1 | 2/2004 | Lee |
| 2004/0044313 A1 | 3/2004 | Nakajima |
| 2004/0049155 A1 | 3/2004 | Schramm |
| 2004/0078003 A1 | 4/2004 | Smith |
| 2004/0092871 A1 | 5/2004 | Knepshield |
| 2004/0106903 A1 | 6/2004 | Shue |
| 2004/0116857 A1 | 6/2004 | Kiehne |
| 2004/0122378 A1 | 6/2004 | Hsu |
| 2004/0138628 A1 | 7/2004 | Woehr |
| 2004/0147876 A1 | 7/2004 | Maggioni |
| 2004/0171989 A1 | 9/2004 | Horner |

(56) References Cited

U.S. PATENT DOCUMENTS

| | | |
|---|---|---|
| 2004/0171995 A1 | 9/2004 | Niermann |
| 2004/0186426 A1 | 9/2004 | Allard |
| 2004/0186427 A1 | 9/2004 | Pok |
| 2004/0186434 A1 | 9/2004 | Harding |
| 2004/0204681 A1 | 10/2004 | Thoresen |
| 2004/0225260 A1* | 11/2004 | Villa et al. ............... 604/164.01 |
| 2004/0230164 A1 | 11/2004 | Spinks |
| 2004/0236288 A1 | 11/2004 | Howell |
| 2004/0236289 A1 | 11/2004 | Ferguson |
| 2004/0243060 A1 | 12/2004 | Rossi |
| 2004/0243061 A1 | 12/2004 | McGurk |
| 2004/0243066 A1 | 12/2004 | Meyer |
| 2004/0243071 A1 | 12/2004 | Suzuki |
| 2005/0004532 A1 | 1/2005 | Woehr |
| 2005/0027263 A1 | 2/2005 | Woehr |
| 2005/0038385 A1 | 2/2005 | Shen |
| 2005/0038399 A1 | 2/2005 | Suzuki |
| 2005/0043691 A1 | 2/2005 | Ferguson |
| 2005/0049554 A1 | 3/2005 | Chueh |
| 2005/0059933 A1 | 3/2005 | Johnson |
| 2005/0070855 A1 | 3/2005 | Ferguson |
| 2005/0075609 A1 | 4/2005 | Latona |
| 2005/0080378 A1 | 4/2005 | Cindrich |
| 2005/0085745 A1 | 4/2005 | Kitta |
| 2005/0096599 A1 | 5/2005 | Crawford |
| 2005/0119627 A1 | 6/2005 | Crawford |
| 2005/0137528 A1 | 6/2005 | Wilkinson |
| 2005/0137535 A1 | 6/2005 | Gollobin |
| 2005/0159706 A1 | 7/2005 | Wilkinson |
| 2005/0182362 A1 | 8/2005 | Sircom |
| 2005/0215951 A1 | 9/2005 | Saulenas |
| 2005/0234408 A1 | 10/2005 | Chong |
| 2005/0240150 A1 | 10/2005 | Gordon |
| 2005/0267412 A1 | 12/2005 | Wilkinson |
| 2006/0058742 A1 | 3/2006 | Cha |
| 2006/0074384 A1 | 4/2006 | Kohler |
| 2006/0079808 A1 | 4/2006 | Allard |
| 2006/0084916 A1 | 4/2006 | Lo |
| 2006/0106339 A1 | 5/2006 | Mastorakis |
| 2006/0106340 A1 | 5/2006 | Goossens |
| 2006/0116638 A1 | 6/2006 | Woehr |
| 2006/0155245 A1 | 7/2006 | Woehr |
| 2006/0161108 A1 | 7/2006 | Mogensen |
| 2006/0161116 A1 | 7/2006 | Willis |
| 2006/0184115 A1 | 8/2006 | Saied |
| 2006/0189934 A1 | 8/2006 | Kuracina |
| 2006/0200195 A1 | 9/2006 | Yang |
| 2006/0217655 A1 | 9/2006 | Vitullo |
| 2006/0229554 A1 | 10/2006 | Lou |
| 2006/0229556 A1 | 10/2006 | Pressly, Sr. |
| 2006/0229563 A1 | 10/2006 | O'Reagan |
| 2006/0253074 A1 | 11/2006 | Thayer |
| 2006/0253076 A1 | 11/2006 | Butts |
| 2006/0264827 A1 | 11/2006 | Whang |
| 2006/0264828 A1 | 11/2006 | Woehr |
| 2007/0005013 A1 | 1/2007 | Lai |
| 2007/0005014 A1 | 1/2007 | Lin |
| 2007/0016139 A1 | 1/2007 | Breitweiser |
| 2007/0038179 A1 | 2/2007 | Bialecki |
| 2007/0038182 A1 | 2/2007 | Bialecki |
| 2007/0038183 A1 | 2/2007 | Bialecki |
| 2007/0038184 A1 | 2/2007 | Bialecki |
| 2007/0038185 A1 | 2/2007 | Albert |
| 2007/0038186 A1 | 2/2007 | Sutton |
| 2007/0038187 A1 | 2/2007 | Albert |
| 2007/0038188 A1 | 2/2007 | Bialecki |
| 2007/0073221 A1 | 3/2007 | Bialecki |
| 2007/0073222 A1 | 3/2007 | Lilley, Jr. |
| 2007/0073225 A1 | 3/2007 | Lee |
| 2007/0078390 A1 | 4/2007 | Cing-hong |
| 2007/0078397 A1 | 4/2007 | Weststrate |
| 2007/0078404 A1 | 4/2007 | Wu |
| 2007/0078405 A1 | 4/2007 | Lai |
| 2007/0078407 A1 | 4/2007 | Huang |
| 2007/0083162 A1 | 4/2007 | O'Reagan |
| 2007/0083167 A1 | 4/2007 | Smith |
| 2007/0100296 A1 | 5/2007 | Hwang |
| 2007/0100297 A1 | 5/2007 | Woehr |
| 2007/0106231 A1 | 5/2007 | Snow |
| 2007/0118082 A1 | 5/2007 | Mori |
| 2007/0135764 A1 | 6/2007 | Chen |
| 2007/0156093 A1 | 7/2007 | Woehr |
| 2007/0156100 A1 | 7/2007 | Moesli |
| 2007/0161950 A1 | 7/2007 | Carlyon |
| 2007/0179443 A1 | 8/2007 | Johnson aka Mindes |
| 2007/0179446 A1 | 8/2007 | Carrez |
| 2007/0197964 A1 | 8/2007 | Hsu |
| 2007/0197965 A1 | 8/2007 | Hsu |
| 2007/0197966 A1 | 8/2007 | Lee |
| 2007/0197967 A1 | 8/2007 | Lee |
| 2007/0219492 A1 | 9/2007 | Lucas |
| 2007/0232998 A1 | 10/2007 | Yang |
| 2007/0250003 A1 | 10/2007 | Bare |
| 2007/0255212 A1 | 11/2007 | Smith |
| 2007/0270753 A1 | 11/2007 | Kulli |
| 2007/0282268 A1 | 12/2007 | Mayse |
| 2008/0021388 A1 | 1/2008 | Schwarzich |
| 2008/0027381 A1 | 1/2008 | Smith |
| 2008/0065015 A1 | 3/2008 | Fiser |
| 2008/0065025 A1 | 3/2008 | Jenkins |
| 2008/0071213 A1 | 3/2008 | Sircom |
| 2008/0071222 A1 | 3/2008 | Rhad |
| 2008/0086089 A1 | 4/2008 | Isaacson |
| 2008/0097304 A1 | 4/2008 | Thorne |
| 2008/0097342 A1 | 4/2008 | Gordin |
| 2008/0097343 A1 | 4/2008 | Woehr |
| 2008/0097344 A1 | 4/2008 | McKinnon |
| 2008/0097345 A1 | 4/2008 | Ferguson |
| 2008/0103449 A1 | 5/2008 | Murashita |
| 2008/0108944 A1 | 5/2008 | Woehr |
| 2008/0115845 A1 | 5/2008 | Leuliet |
| 2008/0119795 A1 | 5/2008 | Erskine |
| 2008/0140011 A1 | 6/2008 | Hager |
| 2008/0147003 A1 | 6/2008 | Menzi |
| 2008/0154195 A1 | 6/2008 | Huang |
| 2008/0177238 A1 | 7/2008 | Follman |
| 2008/0243086 A1 | 10/2008 | Hager |
| 2008/0249478 A1 | 10/2008 | Ishikura |
| 2008/0249480 A1 | 10/2008 | Riesenberger |
| 2008/0283789 A1 | 11/2008 | Rubio |
| 2008/0312596 A1 | 12/2008 | Murashita |
| 2009/0005743 A1 | 1/2009 | Vaillancourt |
| 2009/0012480 A1 | 1/2009 | Moulton |
| 2009/0048566 A1 | 2/2009 | Ferguson |
| 2009/0054852 A1 | 2/2009 | Takano |
| 2009/0082732 A1 | 3/2009 | Hillman |
| 2009/0088696 A1 | 4/2009 | Harding |
| 2009/0093771 A1 | 4/2009 | Hwang |
| 2009/0131876 A1 | 5/2009 | Coyne |
| 2009/0137958 A1 | 5/2009 | Erskine |
| 2009/0143737 A1 | 6/2009 | Kobayashi |
| 2009/0157013 A1 | 6/2009 | Wong |
| 2009/0163861 A1 | 6/2009 | Carlyon |
| 2009/0171285 A1 | 7/2009 | Wang |
| 2009/0177167 A1 | 7/2009 | Kuracina |
| 2009/0182280 A1 | 7/2009 | Glowacki |
| 2009/0216153 A1 | 8/2009 | Srivatsa |
| 2009/0216201 A1 | 8/2009 | Meehan |
| 2009/0227956 A1 | 9/2009 | Emmott |
| 2009/0281499 A1 | 11/2009 | Harding |
| 2009/0281506 A1 | 11/2009 | Mathias |
| 2009/0287154 A1 | 11/2009 | Harding |
| 2009/0292260 A1 | 11/2009 | Vaillancourft |
| 2009/0292261 A1 | 11/2009 | Greene |
| 2009/0306591 A1 | 12/2009 | Amisar |
| 2009/0312711 A1 | 12/2009 | Brimhall |
| 2010/0063455 A1 | 3/2010 | Moyer |
| 2010/0069840 A1 | 3/2010 | Suresh |
| 2010/0082002 A1 | 4/2010 | Baid |
| 2010/0087787 A1 | 4/2010 | Woehr |
| 2010/0106092 A1 | 4/2010 | Tanabe |
| 2010/0114035 A1 | 5/2010 | Schubert |
| 2010/0114036 A1 | 5/2010 | Steyn |
| 2010/0137815 A1 | 6/2010 | Kuracina |

(56) References Cited

U.S. PATENT DOCUMENTS

| | | |
|---|---|---|
| 2010/0191188 A1 | 7/2010 | Harding |
| 2010/0191189 A1 | 7/2010 | Harding |
| 2010/0198152 A1 | 8/2010 | Haindl |
| 2010/0204652 A1 | 8/2010 | Morrissey |
| 2010/0204654 A1 | 8/2010 | Mulholland |
| 2010/0222739 A1 | 9/2010 | Klippenstein |
| 2010/0222745 A1 | 9/2010 | Burkholz |
| 2010/0222746 A1 | 9/2010 | Burkholz |
| 2010/0228197 A1 | 9/2010 | Murashita |
| 2010/0234804 A1 | 9/2010 | Hiejima |
| 2010/0241087 A1 | 9/2010 | Moulton |
| 2010/0249707 A1 | 9/2010 | Woehr |
| 2010/0286611 A1 | 11/2010 | Schraga |
| 2010/0298770 A1 | 11/2010 | Rubinstein |
| 2010/0324484 A1 | 12/2010 | Smith |
| 2010/0331781 A1 | 12/2010 | Millerd |
| 2011/0015573 A1 | 1/2011 | Maan |
| 2011/0015579 A1 | 1/2011 | Swisher |
| 2011/0024664 A1 | 2/2011 | Burnard |
| 2011/0054398 A1 | 3/2011 | Djordjevic |
| 2011/0054402 A1 | 3/2011 | Tanabe |
| 2011/0054403 A1 | 3/2011 | Tanabe |
| 2011/0060286 A1 | 3/2011 | Tanabe |
| 2011/0060294 A1 | 3/2011 | Baid |
| 2011/0066107 A1 | 3/2011 | Stephens |
| 2011/0066197 A1 | 3/2011 | Jaax |
| 2011/0092914 A1 | 4/2011 | Clayson |
| 2011/0098641 A1 | 4/2011 | Haider |
| 2011/0118673 A1 | 5/2011 | Dringenberg |
| 2011/0125056 A1 | 5/2011 | Merchant |
| 2011/0152782 A1 | 6/2011 | Jones |
| 2011/0152832 A1 | 6/2011 | Foshee |
| 2011/0160662 A1 | 6/2011 | Stout |
| 2011/0160663 A1 | 6/2011 | Stout |
| 2011/0160675 A1 | 6/2011 | Ruan |
| 2011/0208124 A1 | 8/2011 | Rhad |
| 2011/0208126 A1 | 8/2011 | Riemelmoser |
| 2011/0208133 A1 | 8/2011 | Woehr |
| 2011/0213307 A1 | 9/2011 | Kawai |
| 2011/0264037 A1 | 10/2011 | Foshee |
| 2011/0264040 A1 | 10/2011 | Li |
| 2011/0275991 A1 | 11/2011 | Thayer |
| 2011/0282285 A1 | 11/2011 | Blanchard |
| 2011/0282286 A1 | 11/2011 | Argentine |
| 2011/0301542 A1 | 12/2011 | Schwartz |
| 2011/0301551 A1 | 12/2011 | Koehler |
| 2011/0319820 A1 | 12/2011 | Teoh |
| 2012/0016301 A1 | 1/2012 | Stout |
| 2012/0016302 A1 | 1/2012 | Stout |
| 2012/0022498 A1 | 1/2012 | Smith |
| 2012/0035552 A1 | 2/2012 | Woehr |
| 2012/0041374 A1 | 2/2012 | Lee |
| 2012/0046620 A1 | 2/2012 | Woehr |
| 2012/0046621 A1 | 2/2012 | Vaillancourt |
| 2012/0059323 A1 | 3/2012 | Moberg |
| 2012/0059325 A1 | 3/2012 | Cluff |
| 2012/0078200 A1 | 3/2012 | Woehr |
| 2012/0130321 A1 | 5/2012 | Woehr |
| 2012/0136311 A1 | 5/2012 | Knutsson |
| 2012/0143138 A1 | 6/2012 | King |
| 2012/0143151 A1 | 6/2012 | Low |
| 2012/0184910 A1 | 7/2012 | Woehr |
| 2012/0197201 A1 | 8/2012 | Tanabe |
| 2012/0215179 A1 | 8/2012 | Halili |
| 2012/0220956 A1 | 8/2012 | Kuracina |
| 2012/0220957 A1 | 8/2012 | Kuracina |

OTHER PUBLICATIONS

U.S. Appl. No. 13/651,979, filed Oct. 15, 2012, Walker et al.
European Search Report dated Jul. 26, 2012 in copending European Appln. No. 12165851.
International Search Report dated Dec. 17, 2012 in copending International Application No. PCT/2012/055295.
International Search Report dated Dec. 19, 2012 in copending International Application No. PCT/US2012/056979.
International Search Report dated Jan. 16, 2013 in copending International Application No. PCT/US2012/060240.

* cited by examiner

SAFETY CATHETER

CROSS-REFERENCE TO RELATED APPLICATIONS

The present application claims the benefit of, and priority to, U.S. Provisional Patent Application Ser. No. 61/539,129, filed on Sep. 26, 2011, the entire contents of which is incorporated by reference herein.

TECHNICAL FIELD

The present disclosure relates to needles for use in medical procedures, and in particular to needle assemblies that include a needle tip guard to cover a tip of a needle to prevent accidental needle sticks.

BACKGROUND

There are a variety of needles available for different medical and surgical uses. For example, intravenous catheters are utilized in various applications for supplying or withdrawing fluids to or from the body. The intravenous catheter includes an external cannula for indwelling in a blood vessel of a patient and an internal needle that is inserted into the external cannula to facilitate smooth piercing of the blood vessel of the patient. In operation, the internal needle is inserted into the external cannula such that the tip portion of the internal needle protrudes from a tip portion of the external cannula. The internal needle is manipulated to pierce a blood vessel and to position the external cannula within the blood vessel. Then, while the external cannula indwells in the blood vessel, the internal needle is withdrawn from the external cannula. With the external cannula positioned within a blood vessel, a medical device can be connected to the rear end portion of the external cannula using, for example, a luer connector, to facilitate the supply and withdrawal of fluid, e.g., blood, medication, etc., to or from the body.

After the internal needle is withdrawn from the external cannula, the exposed needle tip creates a danger of accidental needle stick which can leave a clinician vulnerable to the transmission of various blood-borne pathogens, such as HIV and hepatitis. While needle tip protectors have been developed to protect the clinician from needle stick injuries, the cost, ease of use, and effectiveness of these needle tip protectors leave room for improvement.

Therefore, it would be beneficial to have a needle tip guard that is easily activated by a clinician, adequately protects the clinician from accidental needle stick injury, and is economical to produce.

SUMMARY

A needle assembly in accordance with the present disclosure includes a needle tip guard and needle. The needle tip guard includes a proximal base defining an opening that is dimensioned for passage of the needle therethrough, first and second clamp members extending from the proximal base and defining an internal cavity, and a finger tab extending from the proximal base. Each of the first and second clamp members has an inner surface including a protrusion extending into the internal cavity. A distal end of each of the clamp members includes a clamp arm, the clamp arms being supported for movement between an open position and a closed position. The finger tab includes a contacting portion for engagement by a user. The needle is dimensioned for insertion through the proximal base and clamp members, and includes a needle cannula having a distal portion including at least one indentation dimensioned to receive the protrusion of the clamp members. The needle cannula is positionable between the clamp members to retain the clamp arms in the open position. Receipt of the protrusions within the indentations of the needle allows the clamp arms to move to the closed position.

A catheter and needle assembly in accordance with the present disclosure is also provided. The catheter and needle assembly includes a catheter, a needle, and a needle tip guard. The catheter is configured for placement in a patient and has a catheter hub attached to a proximal end thereof. The needle is dimensioned for insertion into the catheter. The needle has a proximal portion attached to a needle hub and a distal portion terminating in a needle tip. The distal portion also includes at least one indentation. The needle tip guard includes a proximal base defining an opening dimensioned for passage of the needle therethrough, and first and second clamp members extending from the proximal base and defining an internal cavity. Each of the first and second clamp members has an inner surface including a protrusion extending into the internal cavity and a distal end supporting a clamp arm. The clamp arms are supported for movement between an open position in which the needle is positioned between the clamp arms and a closed position in which the protrusions of the clamp members are received within the at least one indentation of the needle when the distal end of the needle is retracted within the internal cavity of the clamp members. A finger tab extends from the proximal base and includes a contacting portion for engagement by a user.

BRIEF DESCRIPTION OF THE DRAWINGS

Various embodiments of the present disclosure will be described herein with references to the accompanying drawings, wherein.

DETAILED DESCRIPTION OF EMBODIMENTS

Various exemplary embodiments of the present disclosure are discussed hereinbelow in terms of a needle and needle tip guard assembly. A needle tip guard in accordance with the present disclosure is utilized with a needle to prevent a clinician from being harmed by a needle tip. The needle tip guard includes first and second clamp members extending from a proximal base and defining an internal cavity therebetween. Each clamp member includes a protrusion extending into the internal cavity. The clamp members are held in an open position by positioning the body of a needle between a distal end of the first and second clamp members. The needle includes at least one indentation on a distal portion thereof such that when the needle is pulled proximally in relation to the needle tip guard the indentation receives the protrusions of the clamp members thereby allowing the clamp members to close about the distal portion of the needle such that the needle tip is enclosed within the internal cavity of the needle tip guard.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

The following discussion includes a description of embodiments of the presently disclosed needle and needle tip guard assembly, as well as a description of exemplary corresponding methods of use in accordance with the principles of the present disclosure.

Figure 1A:
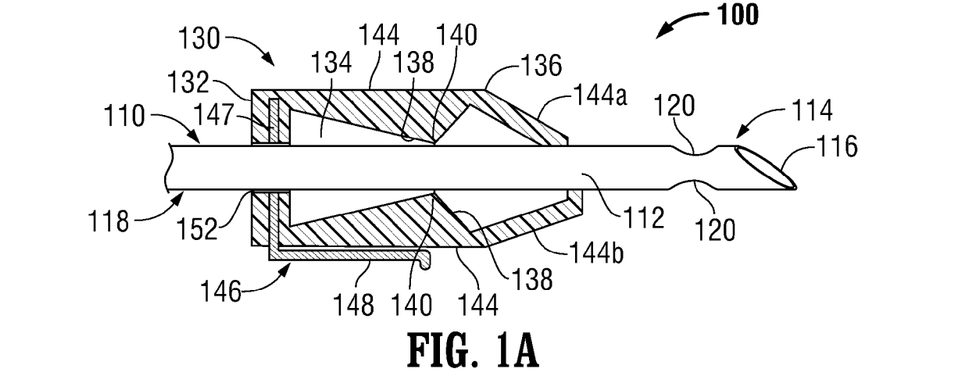
FIGS. 1A and 1B are cross-sectional views of a needle assembly including a needle tip guard in open and closed positions, respectively, in accordance with an embodiment of the present disclosure.
Figure 1B:
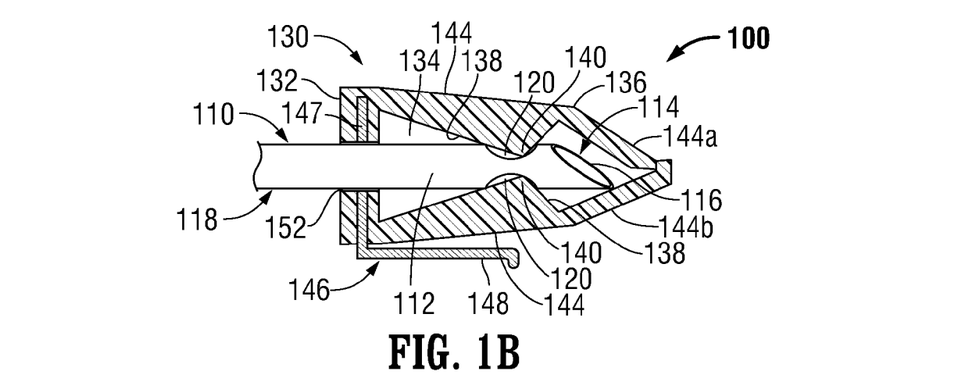
Figure 2:
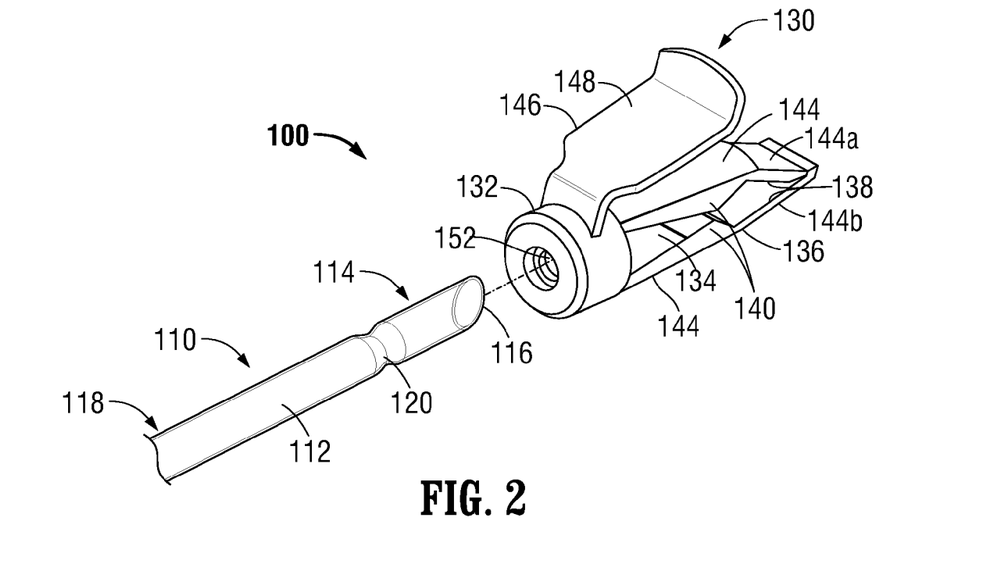
FIG. 2 is a partially exploded perspective view of the needle assembly of FIGS. 1A and 1B.
Figure 3:
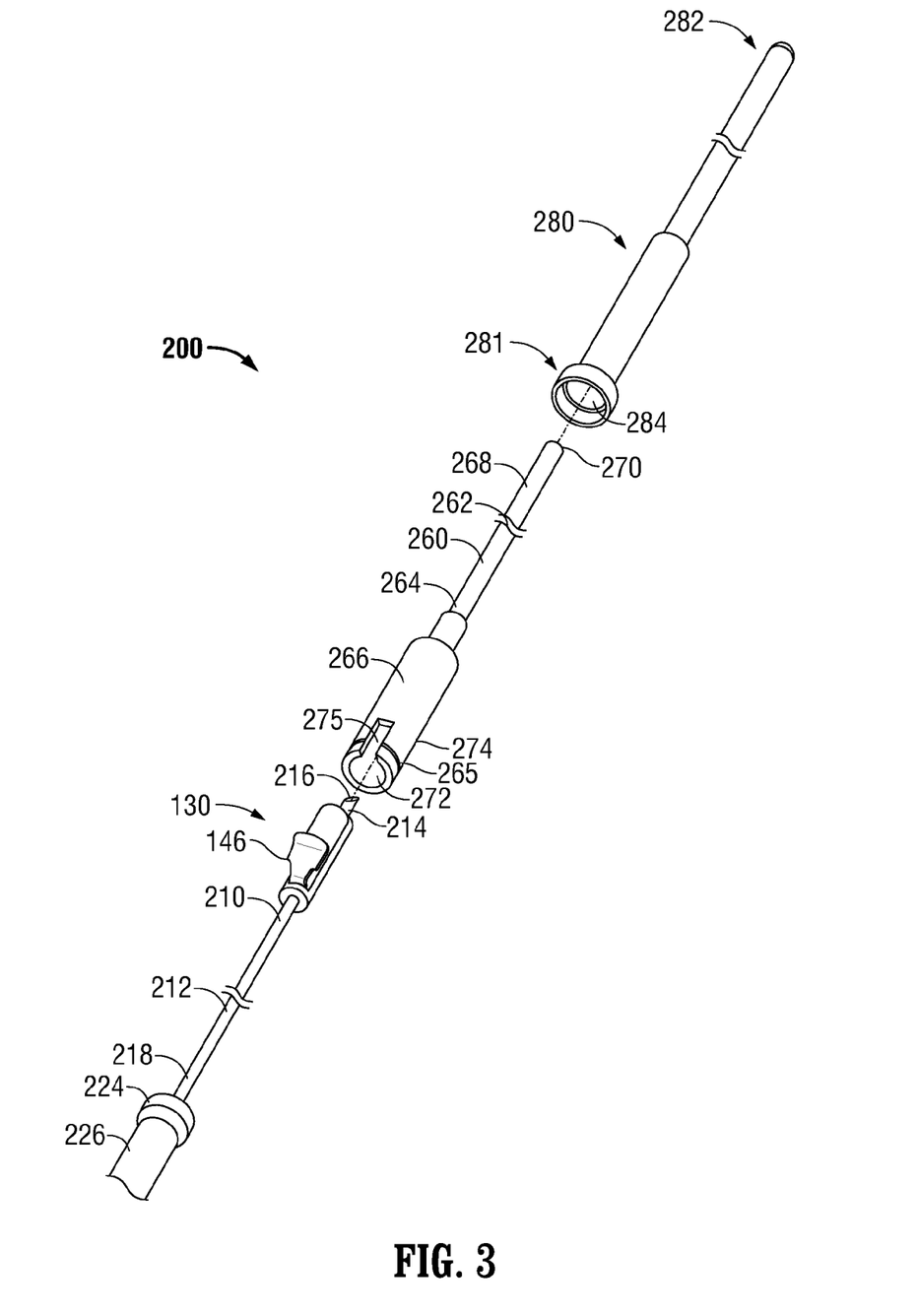
FIG. 3 is an exploded perspective view of a catheter and needle assembly including a needle tip guard and a needle in accordance with an embodiment of the present disclosure.

FIGS. 1A, 1B, and 2 illustrate a needle and needle tip guard assembly 100 including a needle 110 and a needle tip guard 130. Needle 110 includes a needle cannula 112 having a distal portion 114 terminating in a needle tip 116 and a proximal portion 118 adapted to engage a needle hub, e.g., hub 224 (FIG. 3). Distal portion 114 of needle cannula 112 includes at least one indentation 120 formed thereon, e.g., an annular recess or two diametrically disposed indentations. Indentations 120 may be formed by crimping the needle cannula 112 of needle 110, or may be a cut, notch, depression, or other recess for decreasing the effective transverse dimension of the needle 110 relative to the diameter of the needle cannula 112. It is envisioned that the length and gauge of needle 110 may vary depending on the application of use.

Needle tip guard 130 includes a proximal base 132 having first and second clamp members 144 extending therefrom. A cavity 134 extends between a distal end 136 of the clamp members 144 and proximal base 132. An inner surface 138 of each of clamp members 144 includes a protrusion 140 extending into cavity 134 and being received within the indentations 120 of needle 110 as described in further detail below. It is envisioned that protrusions 140 may be defined by bumps, knurls, balls, knobs, or other protuberance configurations that are adapted to receive indentation 120 of needle 110. Distal end 136 of clamp members 144 include clamp arms 144a and 144b supported for movement between an open position (FIG. 1A) and a closed position (FIG. 1B). Clamp members 144 are biased towards a closed position as illustrated in FIG. 1B, such that tension must be provided on the clamp members 144 by the needle cannula 112 of needle 110 to hold the clamp members 144 in the open position as illustrated in FIG. 1A. This bias may be inherent in the material used to construct the needle tip guard 130.

Finger tab 146 is attached to proximal portion of needle tip guard 130 and includes a contacting portion 148 for enabling a clinician to control the needle tip guard 130 with his or her finger. As illustrated, finger tab 146 is secured to proximal base 132 by overmolding proximal base 132 around a proximal end 147 of finger tab 146. It is envisioned that finger tab 146 may be attached to proximal base 132 of needle tip guard 130 via a variety of conventional mechanical and/or chemical means. Alternatively, finger tab 146 may be attached to one or both of the clamp arms 144. In embodiments, contacting portion 148 of finger tab 146 may be textured to improve the grip thereof by a clinician. Contacting portion 148 is spaced from, and extends laterally along, clamp member 144 from the proximal portion 118 toward distal portion 114.

Needle cannula 112 of needle 110 is slidably engaged with needle tip guard 130. As illustrated in FIG. 1A, needle 110 extends distally through needle tip guard 130. More specifically, needle 110 extends through a proximal opening 152 defined in proximal base 132 of needle tip guard 130, through the cavity 134 defined by clamp members 144, and between clamp arms 144a and 144b of clamp members 144. As illustrated in FIGS. 1A and 1B, in one embodiment, clamp arm 144a is positioned proximally of clamp arm 144b.

In use, as distal portion 114 of needle 110 is withdrawn towards proximal base 132, as described in further detail below, indentation or indentations 120 on distal portion 114 of needle 110 receives the protrusions 140 on the inner surface 138 of the clamp members 144, releasing the tension in each of the clamp members 144 and allowing the clamp members 144 to close. A tight fit is created between the indentation 120 of the needle 110 and the protrusion 140 of the needle tip guard 130 thereby increasing the pull-off resistance of the needle tip guard 130 from the needle 110. The different lengths of the clamp arms 144a and 144b ensure closure of the distal end 136 of clamp arms 144a and 144b, and prevent the needle tip 116 from re-emerging therethrough. Alternatively, clamp members 144 may be substantially equal in length.

Figure 4A:
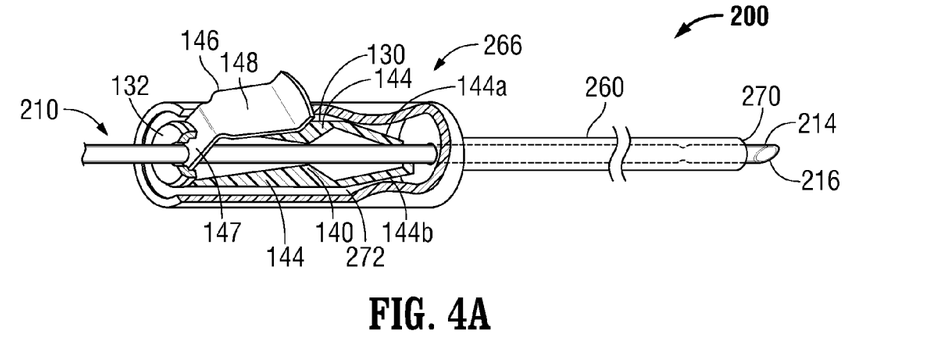
FIG. 4A is a perspective view in partial cross-section of the catheter and needle assembly of FIG. 3 with the needle assembly extending through the catheter and the needle tip guard in an open position in accordance with an embodiment of the present disclosure.
Figure 4B:
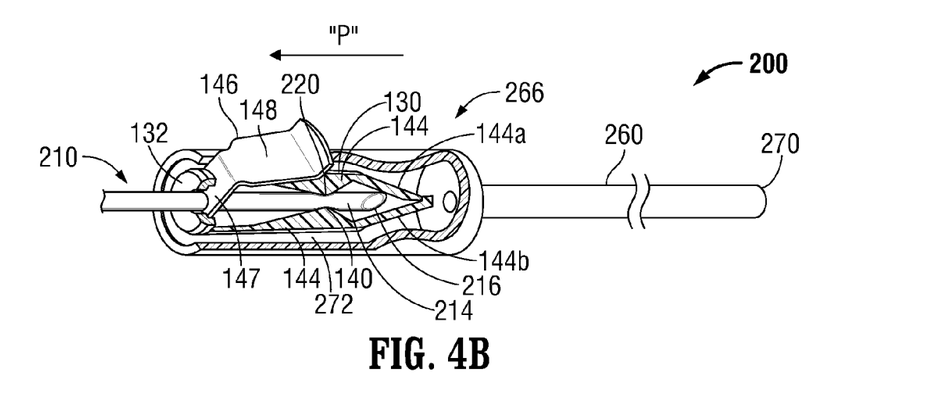
FIG. 4B is a perspective view in partial cross-section of the catheter and needle assembly of FIG. 4A with the needle retracted within the needle tip guard such that the needle tip guard is in a closed position.
Figure 4C:
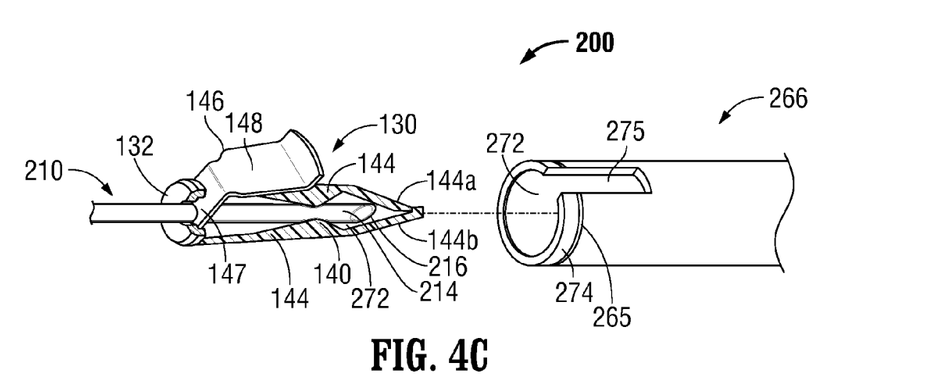
FIG. 4C is a perspective view in partial cross-section of the catheter and needle assembly of FIGS. 4A and 4B with the needle assembly removed from the catheter.

A catheter and needle assembly 200 in accordance with another embodiment of the present disclosure is illustrated in FIGS. 3-4C. Catheter and needle assembly 200 includes a catheter 260 and a needle 210 insertable into an internal channel 262 of catheter 260. The catheter 260 includes a proximal portion 264 connected to a catheter hub 266 and a distal portion 268 terminating in a distal end 270. Catheter 260 is configured to indwell in a blood vessel of a patient for withdrawing blood from the blood vessel or for supplying medicine solutions or other fluids intravenously to the patient. Catheter hub 266 defines an internal chamber 272 dimensioned to receive needle tip guard 130. A proximal end 274 of the catheter hub 266 includes a slot 275 having a generally "U" shaped recess, cut-out, or the like, that is dimensioned to receive finger tab 146. Proximal end 274 is also adapted to engage a medical device, e.g., a syringe or a tubing set (not shown), to administer and/or remove fluids from a blood vessel of a patient via internal chamber 272.

Needle 210 includes a needle cannula 212 having a distal portion 214 terminating in a sharp needle tip 216 and a proximal portion 218 adapted to engage a needle hub 224. Distal portion 214 of needle cannula 212 includes at least one indentation 220 formed, or supported, thereon. The needle hub 224 defines a flash chamber 226 that will fill with blood upon entry into the vein to confirm proper placement of the needle within a vein. Prior to removal of needle 210 from catheter 260, needle tip guard 130 is positioned within internal chamber 272 of catheter hub 266.

As illustrated in FIG. 3, a cap 280 may be provided that includes an open proximal end 281 and a closed distal end 282 defining an internal cavity 284. The open proximal end 281 is releasably connectable to needle hub 224 such that the intervening components of the catheter and needle assembly, i.e., the catheter hub 266, catheter 260, and distal portion 214 of needle 210 extending through catheter 260, are housed within internal cavity 284. The inner diameter of proximal end 281 may be sized and dimensioned to accommodate the outer diameter of the needle hub 224. In embodiments, the proximal end 281 of cap 280 and needle hub 224 are configured to include mating structures to secure cap 280 to needle hub 224, such as by friction or snap fit. Other mechanical means for engaging cap 280 with needle hub 224 may also be employed, such as bayonet coupling, threaded connections, among other conventional male/female fasteners.

The catheter 260, needle 210, needle tip guard 130, and components thereof may be fabricated from any biocompatible material, such as metals like stainless steel, titanium, and aluminum, or polymers like polypropylene, polycarbonate, polyurethane, nylon, silicone, polyether imides, polyether ether ketones, ABS resins, and polyethylene. Alternatively, the components of the catheter and needle assembly 200 may be formed from any biocompatible material having the requisite strength characteristics. Other materials, such as fluororesins may be incorporated into the catheter and needle assembly 200.

In an assembled state, as illustrated in FIG. 4A, needle tip guard 130 is positioned within chamber 272 of catheter hub 266 such that finger tab 146 is received within slot 275 (FIG. 4C) of catheter hub 266 and contacting portion 148 of finger tab 146 is accessible for engagement by a clinician. Needle 210 extends through needle tip guard 130 such that the distal portion 214 of needle 210 extends from distal end 270 of catheter 260. Needle tip guard 130 is retained within internal chamber 272 of catheter hub 266 by application of a force on finger tab 146. Alternatively, other known retention means may be employed, e.g., mechanical couplings such as ribs, frangible connectors, etc. between the needle tip guard 130 and catheter hub 266. When catheter and needle assembly 200 is inserted into a patient, needle tip 216 of needle 210 is utilized to pierce a portion of a tissue of a patient to access and position catheter 260 within a blood vessel.

After catheter 260 is properly positioned within the blood vessel, a clinician may hold catheter hub 266, with a finger placed against contacting portion 148 of finger tab 146, with one hand while pulling needle 210 proximally, in the direction of arrow "P" as illustrated in FIG. 4B, with his or her free hand from the catheter 260. As this occurs, distal portion 214 of needle 210 is pulled from internal channel 262 of catheter 260 and into needle tip guard 130 positioned within internal chamber 272 of catheter hub 266. During proximal movement of needle 210 in relation to clamp members 144, indentations 220 on distal portion 214 of needle 210 receive protrusions 140 of clamp members 144, thereby releasing tension in clamp members 144 such that the clamp arms 144a and 144b are allowed to close around needle tip 216. Needle tip 216 is retained within the needle tip guard 130 to minimize the likelihood of needle stick injury.

The needle tip 216 with the needle tip guard 130 safely disposed thereabout may then be removed from the catheter hub 266, as illustrated in FIG. 4C. Needle 210 may then be safely and properly discarded. After needle 210 has been removed from catheter 260, a medical device, e.g., a syringe, tubing set, etc., may be connected to proximal end 274 of catheter hub 266 via the connector 265, e.g., a luer connector, on the catheter hub 266.

The catheter and needle assembly 200 is not limited to use with blood vessels. It is envisioned that the catheter and needle assembly 200 may be utilized in other areas in a patient's body, such as the thoracic cavity, pleural cavity, gallbladder and liver, renal pelvis, bladder, etc. In such cases, it can be used not only in supplying medicine solutions, etc., to a prescribed area in the human body, but also in removing fluids from the prescribed area in the body.

Figure 5A:
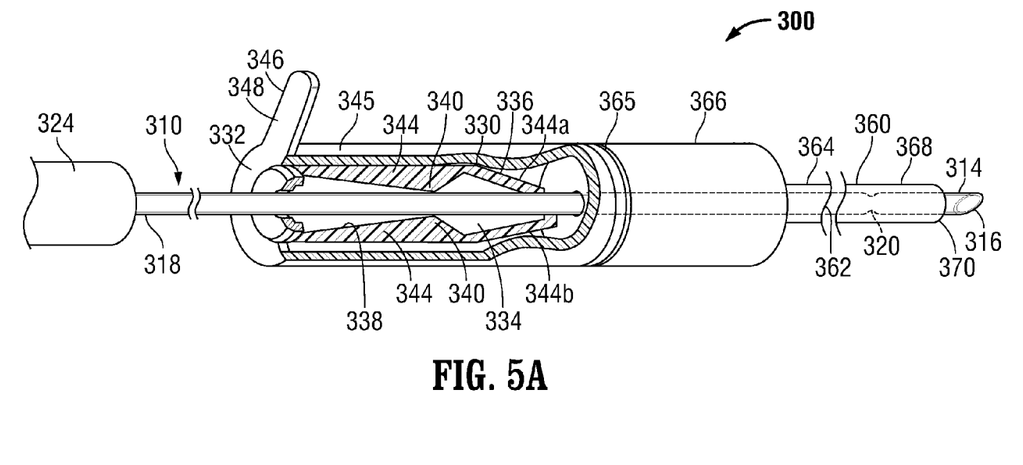
FIG. 5A is a perspective view in partial cross-section of a catheter and needle assembly in accordance with another embodiment of the present disclosure with the needle assembly extending through the catheter and the needle tip guard in an open position.
Figure 5B:
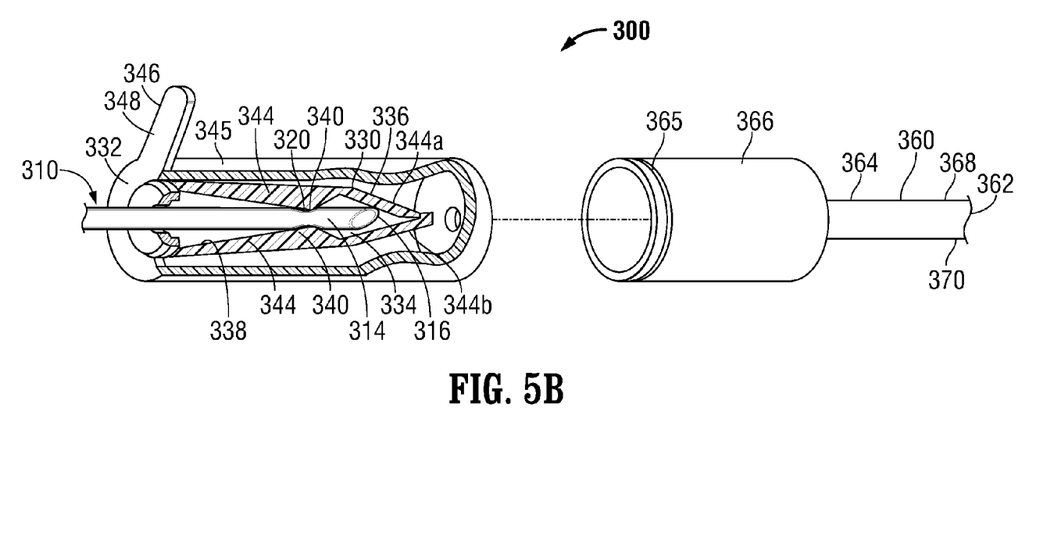
FIG. 5B is a perspective view in partial cross-section of the catheter and needle assembly of FIG. 5A with the needle retracted within the needle tip guard such that the needle tip guard is in a closed position, and the needle assembly separated from the catheter.

Referring now to FIGS. 5A and 5B, an alternate embodiment of a catheter and needle assembly 300 of the present disclosure is illustrated. Catheter and needle assembly 300 is substantially similar to catheter and needle assembly 200 and will only be described with respect to the differences therebetween. Catheter 360 includes a proximal portion 364 connected to a catheter hub 366 and a distal portion 368 terminating in a distal end 370. The needle assembly includes needle 310 and needle tip guard 330. Needle 310 includes a proximal portion 318 adapted to engage needle hub 324, and a distal portion 314 including indentations 320 and terminating in a needle tip 316. Needle tip guard 330 includes proximal base 332 with housing 345 and first and second clamp members 344 extending therefrom. Housing 345 coaxially extends around clamp members 344. A cavity 334 extends between a distal end 336 of the clamp members 344 and proximal base 332. An inner surface 338 of each of clamp members 344 includes a protrusion 340 extending into cavity 334 and being received within the indentations 320 of needle 310. Finger tab 346 extends orthogonally outwardly from proximal base 332 and housing 345. Finger tab 346 includes a contacting portion 348 that may act as a push pad while inserting catheter 360 into a vein and as a pull tab during withdrawal of needle 310 from catheter 360. As illustrated, finger tab 346 is integrally formed with proximal base 332. Housing 345 is dimensioned for positioning between needle hub 324 and catheter hub 366.

In an assembled state, as illustrated in FIG. 5A, needle 310 extends through needle tip guard 330 and catheter 360 such that the distal portion 314 of needle 310 extends from distal end 370 of catheter 360. Needle tip guard 330 abuts catheter hub 366 by application of a force on finger tab 346. When catheter and needle assembly 300 is inserted into a patient, needle tip 316 of needle 310 is utilized to pierce a portion of a tissue of a patient to access and position catheter 360 within a blood vessel. Finger tab 346 may be utilized as a push pad to aid in the insertion of catheter 360 within the blood vessel.

After catheter 360 is properly positioned within the blood vessel, a clinician may hold housing 345 and catheter hub 366 together with one hand, and remove needle 310 from catheter 360 by pulling needle 310 proximally into housing 345 with his or her free hand. As this occurs, distal portion 314 of needle 310 is pulled from internal channel 362 of catheter 360 and into clamp members 344 positioned within housing 345. During proximal movement of needle 310 in relation to clamp members 344, indentations 320 on distal portion 314 of needle 310 receive protrusions 340 of clamp members 344, thereby releasing tension in clamp members 344 such that the clamp arms 344a and 344b are allowed to close around needle tip 316 as illustrated in FIG. 5B. Needle tip 316 is retained within the needle tip guard 330. The needle 310, housed within needle tip guard 330, may then be safely and properly discarded. After needle 310 has been removed from catheter 360, a medical device, e.g., a syringe, tubing set, etc., may be connected to proximal end 374 of catheter hub 366 via the connector 365 on the catheter hub 366.

Persons skilled in the art will understand that the devices and methods specifically described herein, and illustrated in the accompanying drawings, are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosed devices and methods based on the above-described embodiments. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A needle assembly comprising:
   a needle tip guard comprising:
      a proximal base defining an opening dimensioned for passage of a needle therethrough;
      first and second clamp members extending from the proximal base and defining an internal cavity, each of the first and second clamp members having an inner surface including a protrusion extending into the internal cavity and a distal end supporting a clamp arm, the clamp arms being supported for movement between an open position and a closed position; and
      a finger tab extending from the proximal base and including a contacting portion for engagement by a user; and
   a needle dimensioned for insertion through the proximal base and clamp members, the needle having a needle cannula including a distal portion having at least one indentation dimensioned to receive the protrusion of the clamp members, the needle cannula of the needle being positionable between the clamp members to retain the clamp arms in the open position, whereby receipt of the protrusions within the at least one indentation of the needle upon retraction of the distal portion of the needle within the internal cavity of the clamp members allows the clamp arms to move to the closed position.

2. The needle assembly of claim 1, wherein the contacting portion of the finger tab extends laterally along the clamp members in spaced relation therefrom.

3. The needle assembly of claim 1, wherein the finger tab extends orthogonally outwardly from the proximal base.

4. The needle assembly of claim 1, wherein a housing extends from the proximal base coaxially around the first and second clamp members.

5. The needle assembly of claim 1, wherein the clamp members are different lengths.

6. The needle assembly of claim 1, wherein each clamp arm is integrally formed with a respective clamp member.

7. A catheter and needle assembly comprising:
   a catheter configured for placement in a patient, the catheter having a catheter hub attached to a proximal end thereof;
   a needle dimensioned for insertion within the catheter, the needle having a proximal portion attached to a needle hub and a distal portion including at least one indentation, the distal portion terminating in a needle tip; and
   a needle tip guard comprising:
      a proximal base defining an opening dimensioned for passage of the needle therethrough;
      first and second clamp members extending from the proximal base and defining an internal cavity, each of the first and second clamp members having an inner surface including a protrusion extending into the internal cavity and a distal end supporting a clamp arm, the clamp arms being supported for movement between an open position in which the needle is positioned between the clamp arms and a closed position in which the protrusions of the clamp members are received within the at least one indentation of the needle when the distal end of the needle is retracted within the internal cavity of the clamp members; and
      a finger tab extending from the proximal base and including a contacting portion for engagement by a user.

8. The catheter and needle assembly of claim 7, wherein the finger tab is positioned externally of the catheter hub.

9. The catheter and needle assembly of claim 7, wherein the needle tip guard is positioned within the catheter hub.

10. The catheter and needle assembly of claim 9, wherein the catheter hub includes a slot defined in a proximal end thereof and the finger tab is dimensioned to be received within the slot.

11. The catheter and needle assembly of claim 7, wherein the needle tip guard includes a housing extending from the proximal base coaxially around the first and second clamp members.

12. The catheter and needle assembly of claim 11, wherein a distal end of the housing is positioned to abut a proximal end of the catheter hub.

13. The catheter and needle assembly of claim 11, wherein the needle tip guard is positioned between a distal end of the needle hub and a proximal end of the catheter hub.

14. The catheter and needle assembly of claim 7, further comprising a cap including an open proximal end releasably connectable to the needle hub.

* * * * *